United States Patent
Lin et al.

(10) Patent No.: US 9,528,091 B2
(45) Date of Patent: Dec. 27, 2016

(54) LUNG EPITHELIAL PROGENITOR CELLS

(75) Inventors: Joseph H. Lin, Menlo Park, CA (US); Judith A. Shizuru, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 2144 days.

(21) Appl. No.: 12/308,351

(22) PCT Filed: Jun. 18, 2007

(86) PCT No.: PCT/US2007/014296
§ 371 (c)(1),
(2), (4) Date: Oct. 5, 2010

(87) PCT Pub. No.: WO2007/149447
PCT Pub. Date: Dec. 27, 2007

(65) Prior Publication Data
US 2011/0061115 A1    Mar. 10, 2011

Related U.S. Application Data

(60) Provisional application No. 60/814,639, filed on Jun. 16, 2006.

(51) Int. Cl.
*C12N 5/00*     (2006.01)
*C12N 15/85*    (2006.01)
*C12N 5/071*    (2010.01)

(52) U.S. Cl.
CPC .................................. *C12N 5/0689* (2013.01)

(58) Field of Classification Search
CPC ......... C12N 15/85; C12N 1/20; C12N 5/0689; C12N 5/0688; C07H 21/04
See application file for complete search history.

(56) References Cited

U.S. PATENT DOCUMENTS

2007/0025914 A1    2/2007    Jacks et al.

OTHER PUBLICATIONS

Summer et al (Am J Physiol Lung Cell Mol Physiol 285: L97-L104, 2003).*
Summer et al (Am J Physiol Lung Cell Mol Physiol, 287: L477-L483, 2004).*
Chen et al (Lab Invest, 84(6): 727-35, 2004).*
Meneghetti et al (J Histochem Cytochem, 44(10): 1173-1182, 1996.*
Bailey et al (Blood, 103(1): 13-19, 2004.*
Kogler et al (J Exp Med, 200(2): 123-135, 2004.*
Bender; et al., "Identification of Bronchioalveolar Stem Cells in Normal Lung and Lung Cancer", Cell (2005), 121:823-835.
Hilbe; et al., "CD133 positive endothelial progenitor cells contribute to the tumor vasculature in non-small cell lung cancer", J Clin Pathol (2004), 57:965-969.
Lama; et al., "Evidence for tissue-resident mesenchymal stem cells in human adult lung from studies or tranpanted allografts", J. Clinical Investigation (2007), 117(4):989-996.
Phinney; et al., "Concise Review: Mesenchjymal stem/multipotent stromal cells: the state of transf=differentiation and modes of tissue repair-current views", Stem Cells (2007), 25:2896-2902.

\* cited by examiner

*Primary Examiner* — Deborah Crouch
*Assistant Examiner* — Magdalene Sgagias
(74) *Attorney, Agent, or Firm* — Pamela J. Sherwood; Bozicevic, Field & Francis LLP

(57) ABSTRACT

Substantially enriched mammalian lung endothelial and epithelial progenitor cell populations are provided. Methods are provided for the isolation and in vivo differentiation of such lung progenitor cells. The progenitor cells are obtained from lung tissue, including fetal and adult tissues. The cells are useful in transplantation, for experimental evaluation, and as a source of lineage and cell specific products, including mRNA species useful in identifying genes specifically expressed in these cells, and as targets for the discovery of factors or molecules that can affect them.

3 Claims, 9 Drawing Sheets

(9 of 9 Drawing Sheet(s) Filed in Color)

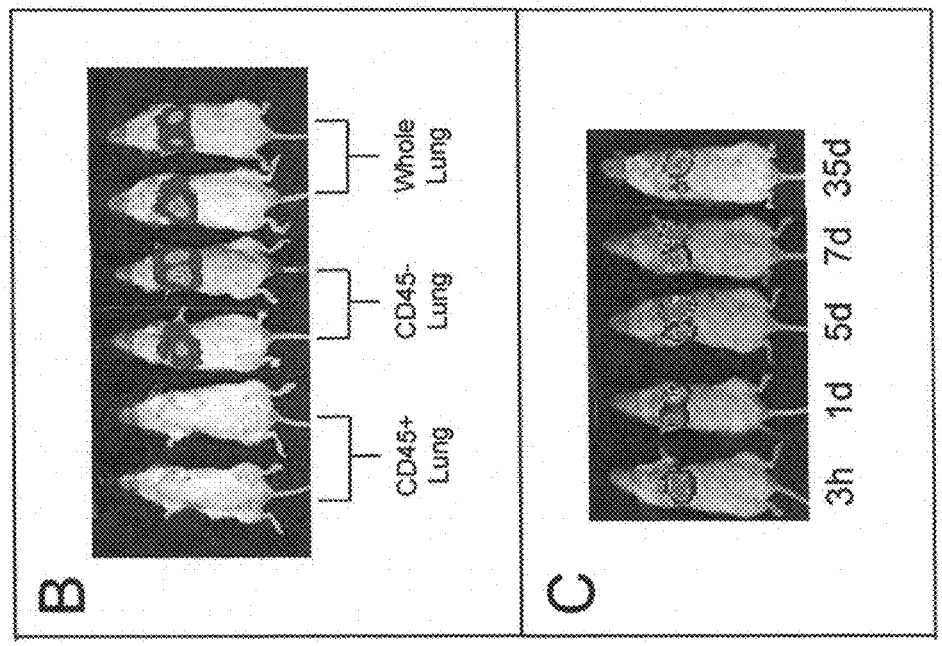
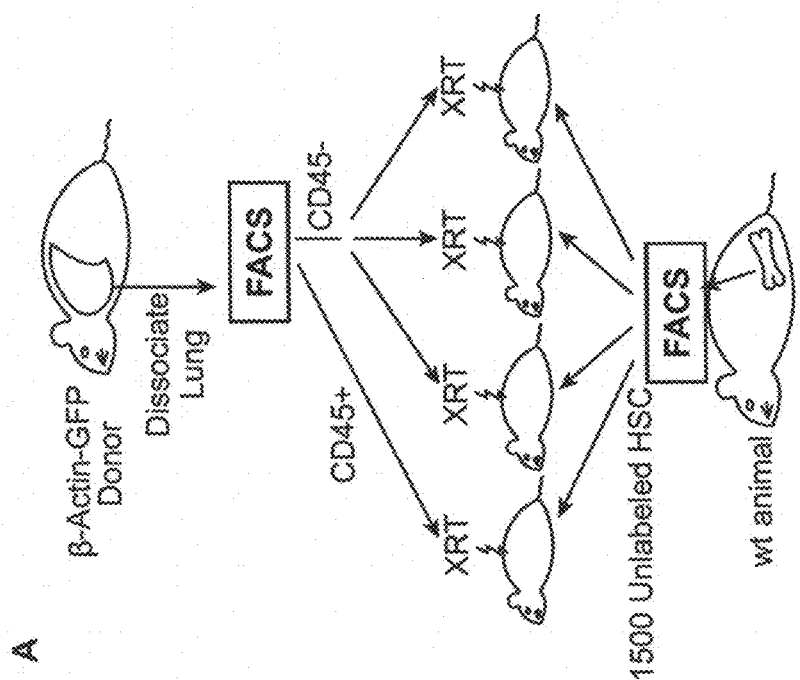
Figure 1

LUNG EPITHELIAL PROGENITOR CELLS

FEDERALLY-SPONSORED RESEARCH OR DEVELOPMENT

This invention was made with Government support under contract HL007948 awarded by the National Institutes of Health. The Government has certain rights in this invention.

INTRODUCTION

The alveoli of the lung have a large surface area, which represents an interface between the environment and bloodstream. As part of homeostasis and response to injury, there is constant repair of this complex structure, in part because the air-exposed lung is subject to an array of potentially damaging agents, including chemical oxidants, bacterial and viral pathogens, proteolytic enzymes, and the like. Such exposure can eventually damage structural components such as elastin and collagen, and contribute to age-related declines in pulmonary function. While repair and maintenance of adult alveoli is not fully understood, it is thought that there is induction of a pool of stem/progenitor cells that proliferate and differentiate into functional tissue.

In the architecturally complex lung, cells of multiple germinal lineages interact both during morphogenesis and to maintain adult lung structure. Even within derivatives of a single germ layer, cells become subdivided into separate cell lineage "zones". For example, the endoderm generates least four distinct epithelial regions, each with a different cellular composition. Additional cell types, including airway smooth muscle, fibroblasts, and the vasculature, are derived from mesoderm. Airway and alveolar architecture, and in turn, function, result from interaction among epithelium, smooth muscle, fibroblasts, and vascular cells, all within an elaborate structural matrix of connective tissue. The complexity has hindered identification of lung stem cells and patterns of cell migration during tissue renewal.

It is hypothesized that a multipotent lung epithelial progenitor gives rise to the two mature alveolar epithelial cell types. Alveolization and microvascular maturation, which represent full differentiation of alveolar epithelial and endothelial tissue begins at gestational age week 36 in humans and continues through the second post-natal year and in mice beginning on postnatal day 0 through 40. Alveolar epithelial and endothelial development occur simultaneously and involve co-regulation and induction. Alveolar epithelial development is characterized by a pattern of proliferation of cuboidal undifferentiated cells that eventually differentiate into the surfactant secreting Type II cells and the flat gas-exchange Type I cells. Alveolar endothelial development (microvascular maturation) follows a pattern whereby a bilayer of capillaries surrounding each alveolus eventually is remodeled into a monolayer, so that adjacent alveoli share one capillary bed, a more efficient arrangement for gas exchange. Whether or not a common progenitor/stem cell pool controls both alveolar generation in developing lung and repair of adult alveoli has yet to be determined.

To achieve a further characterization of lung progenitor cells, and the cells derived therefrom, it is critical to have well defined model systems, that can decipher the complex interplay between "environmental" factors and intrinsic cellular factors that regulate cell renewal, as well as the phenotypic definition of the specific cells capable of giving rise to mature lung cells. Identification and characterization of factors regulating specification and differentiation of cell lineages in the developing and adult lung are of great interest. The further characterization of lung progenitor cells is of great scientific and clinical interest.

PUBLICATIONS

Kim et al. (2005) Cell 121:823-835, "Identification of bronchioalveolar stem cells in normal lung and lung cancer"; Hilbe et al. (2004) J. Clin. Pathol. 57:965-969, "CD133 positive endothelial progenitor cells contribute to the tumour vasculatory on non-small cell lung cancer".

Summer et al., *Embryonic lung side population cells are hematopoietic and vascular precursors*. Am J Respir Cell Mol Biol, 2005. 33(1): p. 32-40 show that a population of embryonic lung cells, isolated by their functional phenotype of effluxing Hoechst dye, can give rise to vascular structures in vitro. Similar findings were reported by Gerritsen et al., *Microvascular endothelial cells from E-selectin-deficient mice form tubes in vitro*. Lab Invest, 1996. 75(2): p. 175-84 using adult lung-derived microvascular endothelial cells. Putative airway stem cells were identified by Giangreco et al. *Terminal bronchioles harbor a unique airway stem cell population that localizes to the bronchoalveolar duct junction*. Am J Pathol, 2002. 161(1): p. 173-82 by their anatomic locations and resistance to injury. Pluripotent stem cells capable of lung regeneration existing elsewhere in the body has been proposed by investigators studying the capability of bone marrow-derived cells to repair lung and other tissues Krause et al. Cell, 2001. 105(3): p. 369-77; and Herzog et al. Stem Cells, 2006. 24(8): p. 1986-92. Whether such bone marrow cells truly represent multipotent stem cells or cells capable of transdifferentiation has been seriously challenged, for example see Wagers et al. Science, 2002. 297 (5590): p. 2256-9; Kotton et al. Am J Respir Cell Mol Biol, 2005. 33(4): p. 328-34; Chang et al. Am J Respir Cell Mol Biol, 2005. 33(4): p. 335-42 and Harris et al. Science, 2004. 305(5680): p. 90-3.

SUMMARY OF THE INVENTION

Methods and compositions are provided for the separation and characterization of lung progenitor cells. Progenitor cell populations provided herein are endothelial or epithelial progenitor cells having the ability to engraft the lung in vivo and which give rise to differentiated lung cells. The cells are derived from lung tissue, and may be separated from other cells, e.g. differentiated cells present in the lung, by expression of specific cell surface markers. The cells are useful in transplantation, for experimental evaluation, and as a source of lineage and cell specific products, including mRNA species useful in identifying genes specifically expressed in these cells, and as targets for the discovery of factors or molecules that can affect them.

In vitro and in vivo systems are provided for the growth and analysis, including clonal analysis, of lung progenitor cells. In particular, the endothelial progenitor cells of the invention are shown to specifically home to, and durably engraft in injured recipient lungs in vivo, where clusters of contiguous cells are formed from the progenitors.

In some embodiments of the invention, methods are provided for engraftment of lung epithelial cells, where the cells are delivered to the respiratory system in an excipient of lung surfactant, which may be endogenous, synthetic, etc. The epithelial progenitor cell populations engraft following tracheal delivery.

The lung progenitor cells find use in the evaluation of therapies relating to lungs. The cells also find use in toxicology testing, for the production of lungs in culture, for evaluation of lung pathogens, e.g. *M. tuberculosis*, inter alia.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1. Donor-derived lung cells home to and engraft in injured recipient lungs in vivo. A) Shows the experimental schematic for co-transplantation studies. B) Only $CD45^-$ lung cells home to injured lung. β-actin luciferase lung cells were injected into lethally-irradiated recipient mice and whole body luminescence was detected at 1 hour following tail vein intravenous injection. Left two animals received $CD45^+$ cells ($4\times10^5$); middle two animals received $CD45^-$ cells ($4\times10^5$) and right two animals received unfractionated lung cells ($2.4\times10^6$). C) $CD45^-$ lung cells persist in injured recipient lungs. A representative recipient mouse (of 10 mice) transplanted with $10^6$ $CD45^-$ β-actin luciferase lung cells plus unlabeled whole bone marrow was serially imaged up to 35 days.

DESCRIPTION OF THE SPECIFIC EMBODIMENTS

Figure 2:
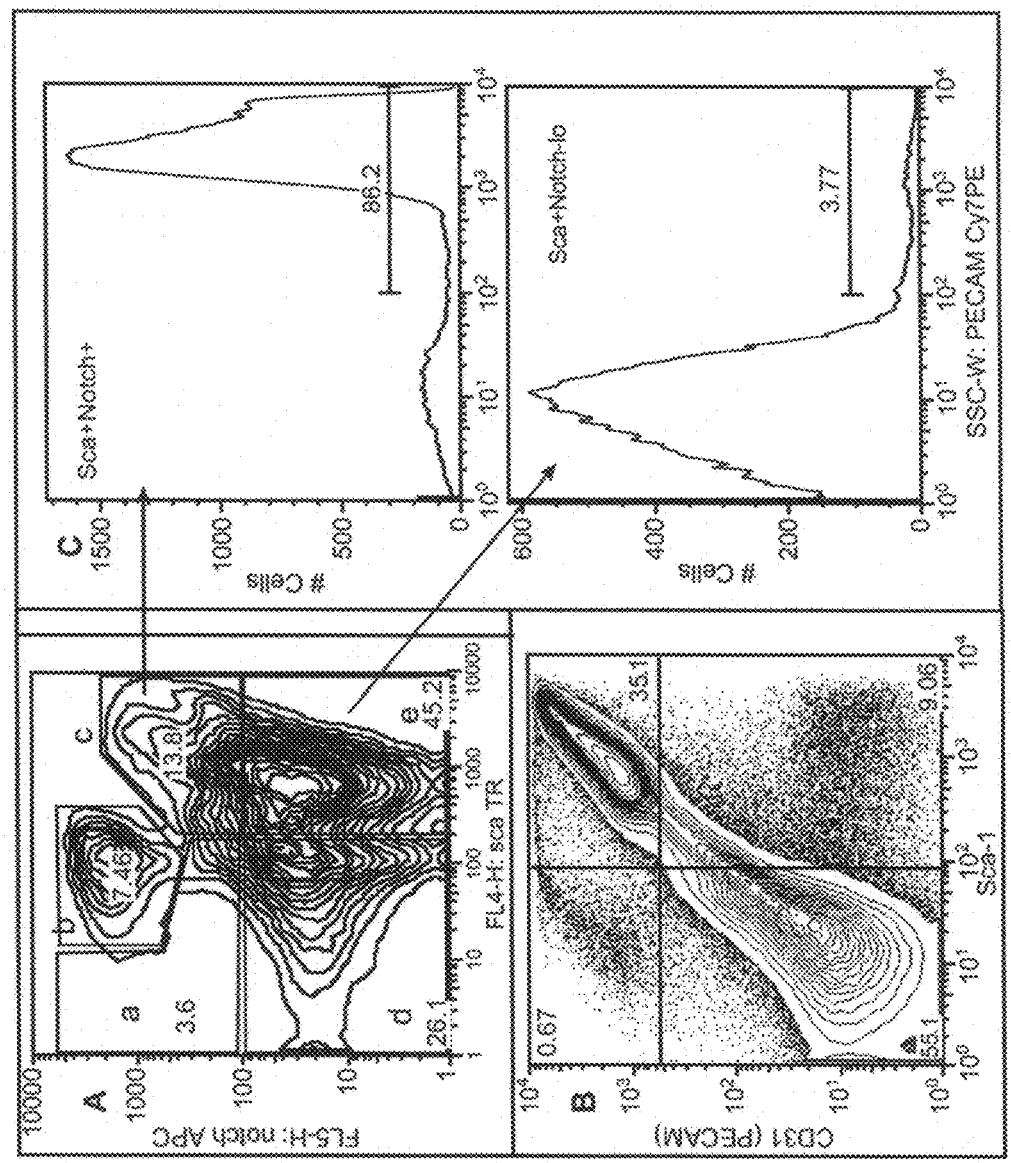
FIG. 2. Staining profile of the CD45− fraction of dissociated lung cells from a 4 week old animal for Sca-1, Notch1. A) The $CD45^-$ fraction of lung cells was stained for Sca-1 and Notch1 yielding five distinct populations labeled a through e as follows: a: Sca-1$^-$ Notch1$^+$, b: Sca-1$^{lo}$Notch1$^+$, c: Sca-1$^+$Notch1$^+$, d: Sca-1$^{-1}$Notch1$^{-/lo}$, e: Sca-1$^+$Notch1$^{-/lo}$. B) CD31 vs. Sca-1 FACS plot of the CD45− lung population shows that >98% of the CD31+ cells are Sca-1+. C) Histograms of CD31 staining in the Sca-1$^+$ Notch1$^+$ and Sca-1$^+$Notch1$^{-/lo}$ populations.

Lung progenitor cells are isolated and characterized, and demonstrated to be progenitor cells capable of developing into differentiated lung tissue when transplanted in vivo, including alveolar endothelial cells. The cell populations enriched for lung progenitor cells are useful in transplantation to provide a recipient with restoration of lung function; for drug screening; in vitro and in vivo models of lung development; in vitro and in vivo screening assays to define growth and differentiation factors, and to characterize genes involved in lung development and regulation; and the like. The native cells may be used for these purposes, or they may be genetically modified to provide altered capabilities.

The lung endothelial progenitor cell is shown herein to be capable of homing to, engraftment and expansion in recipient lungs in vivo. For engraftment, the cells may be delivered by a variety of routes, e.g. by parental administration. Lung epithelial progenitor cells provided herein can be delivered to the lung for engraftment by an endotracheal route.

The ability to develop into regenerating lungs can be assessed in vivo, e.g. in immunodeficient animals, e.g. RAG, SCID, nude, etc., with allogeneic, syngeneic or xenogeneic donor cells, by the ability of these donor cells to provide functionality in this system. Of particular interest are animals having injured lungs, e.g. following radiation exposure. Alternatively, in vitro methods may be used for the assessment of biological function, by the cultivation of with appropriate growth factors and/or cytokines.

The lung progenitor cells are positively and/or negatively selected for expression of specific markers. By flow cytometry analysis and sorting of cell surface markers, such as those described below, viable cells can be sorted. The cells may be selected for low expression of Notch-1. Additionally, the cells may also be negatively selected, or characterized as negative for, expression of CD45. The progenitor cell population of CD45$^-$ Notch$^{-/low}$ cells may also be selected for expression one or more of CD133 and/or Sca-1.

Epithelial progenitor cell populations are also provided. One such population is characterized as being CD45$^-$Sca-1$^-$. This population initially engrafts as Type II epithelial cells, but generates Type I epithelial cells after a period of time following transplantation. Another epithelial progenitor cell population is characterized as CD45$^-$PECAM$^-$T1α$^+$. Epithelial progenitor cells can be delivered to the distal lung (alveolar compartment) via an endotracheal route, preferably using lung surfactant as an excipient.

DEFINITIONS

In the definitions of markers and cells provided below, the terms will typically be defined in terms of human proteins, cells, and the like, where human cells are a preferred embodiment of the invention. It will be understood by those of skill in the art that other mammals may also be used as a source of cells, and that selection of cells from such non-human species will utilize the counterpart homologous and functionally related markers for that species.

Lung engraftment. As used herein, the term "lung progenitor cells"—refers to a progenitor cell population that, when transplanted into an animal, gives rise to differentiated lung tissue. The developmental potential of lung progenitor cells can be assessed by functional and phenotypic criteria, including staining with antibodies specific for endothelial and epithelial markers, histochemistry, immunohistochemistry, and the like.

Positive and negative staining. The subject lung progenitor cells are characterized by their expression of cell surface markers. While it is commonplace in the art to refer to cells as "positive" or "negative" for a particular marker, actual expression levels are a quantitative trait. The number of molecules on the cell surface can vary by several logs, yet still be characterized as "positive". It is also understood by those of skill in the art that a cell which is negative for staining, i.e. the level of binding of a marker specific reagent is not detectably different from a control, e.g. an isotype matched control; may express minor amounts of the marker. Characterization of the level of staining permits subtle distinctions between cell populations.

The staining intensity of cells can be monitored by flow cytometry, where lasers detect the quantitative levels of fluorochrome (which is proportional to the amount of cell surface marker bound by specific reagents, e.g. antibodies). Flow cytometry, or FACS, can also be used to separate cell populations based on the intensity of binding to a specific reagent, as well as other parameters such as cell size and light scatter. Although the absolute level of staining may differ with a particular fluorochrome and reagent preparation, the data can be normalized to a control.

In order to normalize the distribution to a control, each cell is recorded as a data point having a particular intensity of staining. These data points may be displayed according to a log scale, where the unit of measure is arbitrary staining intensity. In one example, the brightest stained cells in a sample can be as much as 4 logs more intense than unstained cells. When displayed in this manner, it is clear that the cells falling in the highest log of staining intensity are bright, while those in the lowest intensity are negative. The "low" positively stained cells have a level of staining above the brightness of an isotype matched control, but is not as intense as the most brightly staining cells normally found in the population. Low positive cells may have unique properties that differ from the negative and brightly stained positive cells of the sample. An alternative control may utilize a substrate having a defined density of marker on its surface, for example a fabricated bead or cell line, which provides the positive control for intensity.

Sources of Progenitor Cells. Ex vivo and in vitro cell populations useful as a source of cells may include fresh or frozen lung cell populations, etc. obtained from embryonic, fetal, pediatric or adult tissue. The methods can include further enrichment or purification procedures or steps for cell isolation by positive selection for other cell specific markers. The progenitor cells may be obtained from any mammalian species, e.g. human, equine, bovine, porcine, canine, feline, rodent, e.g. mice, rats, hamster, primate, etc.

Isolation of Lung Progenitor Cells

The subject lung progenitor cells of the invention are separated from a complex mixture of lung cells by techniques that enrich for cells having the characteristics as described. The endothelial progenitor cells are characterized by low expression of Notch1 and for negative expression of CD45. In the mouse the endothelial progenitor cells are further characterized as being Sca-1 positive. In the human, the endothelial progenitor cells may be further characterized by expression of CD133.

The epithelial progenitor cells are characterized as $CD45^-$ Sca-1, or as $CD45^- PECAM^- T1\alpha^+$.

The source of lung cells may be a fetal or post-natal mammal, e.g. neonatal, juvenile, adult, etc. The cells may be fresh or frozen. Mammalian tissue sources include primates, e.g. humans, etc., and laboratory animals; e.g. rats, mice, rabbits, etc.

For isolation of cells from tissue, an appropriate solution may be used for dispersion or suspension. Such solution will generally be a balanced salt solution, e.g. normal saline, PBS, Hanks balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The tissue may be enzymatically and/or mechanically dissociated. In some embodiments the lung tissue is treated with a gentle protease, e.g. dispase, etc., for a period of time sufficient to dissociate the cells, then is gently mechanically dissociated.

An initial separation may select for cells by various methods known in the art, including elutriation, Ficoll-Hypaque or flow cytometry using the parameters of forward and obtuse scatter.

Separation of the subject cell population will then use affinity separation to provide a substantially pure population. Techniques for affinity separation may include magnetic separation, using antibody-coated magnetic beads, affinity chromatography, cytotoxic agents joined to a monoclonal antibody or used in conjunction with a monoclonal antibody, e.g. complement and cytotoxins, and "panning" with antibody attached to a solid matrix, e.g. plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (propidium iodide, 7-AAD). Any technique may be employed which is not unduly detrimental to the viability of the selected cells.

The affinity reagents may be specific receptors or ligands for the cell surface molecules indicated above. Of particular interest is the use of antibodies as affinity reagents. The details of the preparation of antibodies and their suitability for use as specific binding members are well known to those skilled in the art. Depending on the specific population of cells to be selected, antibodies having specificity for one or more of: CD45; Notch; Sca-1; CD133; PECAM (CD31); T1α are contacted with the starting population of lung cells.

As is known in the art, the antibodies will be selected to have specificity for the relevant species, i.e. antibodies specific for human CD45 are used for selection of human cells; antibodies specific for mouse Sca-1 are used in the selection of mouse cells, and the like.

Conveniently, these antibodies are conjugated with a label for use in separation. Labels include magnetic beads, which allow for direct separation, biotin, which can be removed with avidin or streptavidin bound to a support, fluorochromes, which can be used with a fluorescence activated cell sorter, or the like, to allow for ease of separation of the particular cell type. Fluorochromes that find use include phycobiliproteins, e.g. phycoerythrin and allophycocyanins, fluorescein and Texas red. Frequently each antibody is labeled with a different fluorochrome, to permit independent sorting for each marker.

The antibodies are added to a suspension of cells, and incubated for a period of time sufficient to bind the available cell surface antigens. The incubation will usually be at least about 5 minutes and usually less than about 30 minutes. It is desirable to have a sufficient concentration of antibodies in the reaction mixture, such that the efficiency of the separation is not limited by lack of antibody. The appropriate concentration is determined by titration. The medium in which the cells are separated will be any medium which maintains the viability of the cells. A preferred medium is phosphate buffered saline containing from 0.1 to 0.5% BSA. Various media are commercially available and may be used according to the nature of the cells, including Dulbeccos Modified Eagle Medium (dMEM), Hank's Basic Salt Solution (HBSS), Dulbeccos phosphate buffered saline (dPBS), RPMI, Iscoves medium, PBS with 5 mM EDTA, etc., frequently supplemented with fetal calf serum, BSA, HSA, etc.

The labeled cells are then separated as to the phenotype described above. The separated cells may be collected in any appropriate medium that maintains the viability of the cells, usually having a cushion of serum at the bottom of the collection tube. Various media are commercially available and may be used according to the nature of the cells, including dMEM, HBSS, dPBS, RPMI, Iscoves medium, etc., frequently supplemented with fetal calf serum.

Compositions highly enriched for lung progenitor activity are achieved in this manner. The subject population will be at or about 50% or more of the cell composition, and usually at or about 90% or more of the cell composition, and may be as much as about 95% or more of the live cell population. The enriched cell population may be used immediately, or may be frozen at liquid nitrogen temperatures and stored for long periods of time, being thawed and capable of being reused. The cells will usually be stored in 10% DMSO, 50% FCS, 40% RPMI 1640 medium. Once thawed, the cells may be expanded by use of growth factors and/or stromal cells for proliferation and differentiation.

The present methods are useful in the development of an in vitro or in vivo model for lung functions and are also useful in experimentation on gene therapy and for artificial organ construction. The developing lungs serve as a valuable source of novel growth factors and pharmaceuticals and for the production of viruses or vaccines, as well as for the study of lung pathogens, e.g. *M. tuberculosis*, for in vitro toxicity and metabolism testing of drugs and industrial compounds, for gene therapy experimentation, for the construction of artificial transplantable lungs, and for lung mutagenesis and carcinogenesis studies.

In Vivo Models

Analysis of lung progenitor cell populations may utilize an in vivo model for lung development of endothelial and epithelial cells. Such a model will generally involve an animal in which a niche for lung progenitor cells has been made available for engraftment; and a population of donor cells selected by the methods described herein. Damage to a tissue creates a potential space where parenchymal cells are missing. Such a space results in a regenerative niche; a niche wherein stem/progenitor cells may home to, proliferate and then differentiate into functional cells. The progenitor cells can be administered via the airway, e.g. by tracheal administration, in order to address epithelial cell development, or through a systemic route, e.g. intra-venous, etc. to address endothelial development.

In some embodiments, an in vivo model utilizes a recipient animal that has been exposed to myeloablative radiation, e.g. at around 9.5 Gy. Radiation injury to lung tissue has been well documented in humans and rodents. Following radiation, initial endothelial damage likely precedes, and may even potentiate epithelial damage. Endothelial injury results in increased vascular permeability followed by increased alveolar protein fluid concentrations. In mice, increased alveolar fluid concentration of albumin and fibrinogen are observed one week following radiation. Thus, while radiation damages both endothelium and epithelium, it damages endothelium first. Because myeloablative radiation also destroys recipient hematopoiesis, irradiated recipients may require rescue with unmarked hematopoietic stem cells, as is known in the art.

In another embodiment, the in vivo model makes a niche available by chemical damage to the lung. Sources of chemical damage include tracheal instillation of elastase, which recapitulates the excess proteolytic activity that is important in the pathogenesis of cigarette smoke-induced emphysema in humans. In mice, significant emphysema is noted three weeks after intra-tracheal administration of elastase. The elastase is cleared within 24 hours, but it sets off a cascade of injury. The initial insult is to the epithelium, followed by endothelial injury. This series of events occurs in reverse order for what has been described for radiation induced injury. Various morphometric analyses can be performed, but an accepted, standardized quantification of emphysematous lung injury is the mean linear intercept score of lung histologic sections. Alternatively the animals can be induced to produce antibodies against endothelial cells, where emphysema forms to a similar degree as intra-tracheal elastase-induced emphysema.

In another embodiment, monocrataline injection is used to create chemical damage. Injection of monocrataline in mice and rats creates lung endothelium specific injury that causes pulmonary hypertension. Intratracheal bleomycin administration provides another means of damaging the lungs, in which the damage leads to pulmonary fibrosis and injury to both the endothelium and epithelium of the alveolus.

For experimental purposes it is preferable to use a donor cell population that comprises a detectable marker, e.g. an allotypic marker that distinguishes the donor cells from recipient cells; a bioluminescence marker, e.g. green fluorescent protein, luciferase, etc.; and the like. In a preferred embodiment of the invention, the detectable marker operably linked to a promoter active in lung cells. By "operably linked" is meant that a DNA sequence and a regulatory sequence(s) are connected in such a way as to permit gene expression when the appropriate molecules, e.g. transcriptional activator proteins, are bound to the regulatory sequence(s). The native gene encoding green fluorescent protein has been cloned from the bioluminescent jellyfish *Aequorea victoria* (Morin, J. et al., J Cell Physiol (1972) 77:313-318). The availability of the gene has made it possible to use GFP as a marker for gene expression. GFP itself is a 283 amino acid protein with a molecular weight of 27 kD. It requires no additional proteins from its native source nor does it require substrates or cofactors available only in its native source in order to fluoresce. GFP-S65T (wherein serine at 65 is replaced with threonine) may be used, which has a single excitation peak at 490 nm. (Heim, R. et al., Nature (1995) 373:663-664); U.S. Pat. No. 5,625,048. Other mutants have also been disclosed by Delagrade, S. et al., Biotechnology (1995) 13:151-154; Cormack, B. et al., Gene (1996) 173:33-38 and Cramer, A. et al. Nature Biotechnol (1996) 14:315-319. Additional mutants are also disclosed in U.S. Pat. No. 5,625,048. By suitable modification, the spectrum of light emitted by the GFP can be altered. Thus, although the term "GFP" is used in the present application, the proteins included within this definition are not necessarily green in appearance.

It is found that endothelial progenitor cells as described herein will home to and engraft in the lungs following systemic administration, e.g. by tail vein injection, etc. The epithelial progenitor cell populations described herein engraft in the lungs following tracheal administration, usually in formulated in lung surfactant for delivery. The engraftment can be assessed by in vivo or in vitro tracking of marked cells; and can be further assessed by examining the lungs histologically or immunohistologically for the appearance of donor cells forming lung specific structures, including epithelial and endothelial cells.

In Vitro Cell Culture

The enriched cell population may be grown in vitro under various culture conditions. Cultures may be designed to promote cell expansion and/or cell differentiation. Culture medium may be liquid or semi-solid, e.g. containing agar, methylcellulose, etc. The cell population may be conveniently suspended in an appropriate nutrient medium, such as Iscove's modified DMEM, RPM-1640, M199, etc., normally supplemented with fetal calf serum (about 5-10%), L-glutamine, a thiol, particularly 2-mercaptoethanol, and antibiotics, e.g. penicillin and streptomycin. The culture substrate may include a coated surface for cell growth, e.g. fibronectin, matrigel; collagen; etc.

The progenitor cells may be grown in the presence of growth factors. Factors of interest for expansion of lung progenitor cells include plated BEGF, basic fibroblast growth factor, insulin-like growth factor, endothelial cell growth factor, VEGF, etc. The factors may be the products of other cell types, for example, expressed proteins associated with a disease, may be compounds that simulate naturally occurring factors, may be surface membrane proteins free of the membrane or as part of microsomes, or other reagent that induces the appropriate pathway to aid in the simulation of the phenotype or provides the appropriate environment to simulate the physiological condition. The factors (including mimetics thereof) may be added individually or in combination, from feeder cells, may be added as a bolus or continuously, where the factor is degraded by the culture, etc. Naturally occurring factors may be isolated from natural sources or produced by recombinant technology or synthesis, compounds that mimic the action of other compounds or cell types, e.g. an antibody which acts like a factor or mimics a factor, such as synthetic drugs that act as ligands for target receptors. Where a family of related factors are referred to with a single designation, e.g. IL-1, VEGF, IFN, etc., in referring to the single description, any one or some or all of the members of the group are intended, where the literature will be aware of how the factors are to be used in the context of the culture.

Variation in culture conditions may be used to elicit specific effects. Relative hypoxia in an incubator condition may preserve an undifferentiated state. Different extracellular matrix coated plastic may change how the EPCs proliferate and differentiate. And since the alveolus is a specialized anatomic site that stretches with each inflation, growth on stretchable membranes sitting on an air-fluid interface may better simulate their in vivo niche.

The subject cells may be grown in a co-culture with feeder layer cells. Cells that can be used as a feeder layer include stromal cells, fibroblasts derived from human or other animal sources; fetal fibroblasts derived by primary culture from the same species as the lung; the STO fibroblast cell line; etc. These cell layers provide non-defined components to the medium and may restrain the differentiation of the pluripotent cells. Culture in the presence of feeder layers is particularly useful for clonal culture, i.e. where a single progenitor cell is expanded to a population.

Functional assays may be performed using in vitro cultured cells, particularly clonogenic cultures of cells. For example, cultured cells may be assessed for their ability to express lung specific proteins.

The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors. The specific culture conditions are chosen to achieve a particular purpose, i.e. maintenance of progenitor cell activity, etc. In addition to, or instead of growth factors, the subject cells may be grown in a co-culture with stromal or feeder layer cells. Feeder layer cells suitable for use in the growth of progenitor cells are known in the art.

The subject co-cultured cells may be used in a variety of ways. For example, the nutrient medium, which is a conditioned medium, may be isolated at various stages and the components analyzed. Separation can be achieved with HPLC, reversed phase-HPLC, gel electrophoresis, isoelectric focusing, dialysis, or other non-degradative techniques, which allow for separation by molecular weight, molecular volume, charge, combinations thereof, or the like. One or more of these techniques may be combined to enrich further for specific fractions that promote progenitor cell activity.

The lung progenitor cells may be used in conjunction with a culture system in the isolation and evaluation of factors associated with the differentiation and maturation of lungs. Thus, the cells may be used in assays to determine the activity of media, such as conditioned media, evaluate fluids for growth factor activity, involvement with formation of specific structures, or the like. Cultures may also be used as a means of processing drugs and other compounds, to determine the effect of lung metabolism on an agent of interest. For example, the product of lung metabolism may be isolated and tested for toxicity and efficacy.

Transplantation

The subject cells may be used for reconstitution of lung function in a recipient by parenteral or tracheal administration of the cells. Tracheal administration, e.g. of epithelial progenitor cells, may utilize surfactant as a delivery vehicle.

Endogenous surfactant is a complex mixture of 80% phospholipids, 8% neutral phospholipids, and 12% protein (see Jobe (1993) Pulmonary surfactant therapy. N Engl J Med. 328:861-8, herein specifically incorporated by reference). Some 60% of the phospholipid component is saturated phosphatidylcholine, of which 80% is dipalmitoyl-phosphatidylcholine (DPPC). Unsaturated phosphatidylcholine comprises another 25% of the phospholipid component, and the remaining 15% consists of phosphatidylinositol and phosphatidylglycerol. Although DPPC, the primary phospholipid, markedly reduces surface tension, it does not spread easily because of its poor adsorption. For this reason, a surfactant matrix formed with DPPC and proteins is essential. The protein component is composed of the hydrophilic surfactant protein (SP) A (SP-A) and SP-D, complex glycoproteins, and at least two hydrophobic surfactant proteins (SP-B and SP-C). The SPs are synthesized and secreted by type II alveolar cells. Because these hydrophobic proteins lower surface tension and enhance adsorption and spreading at the air-liquid interface, they are critical for the surfactant activity of phospholipids.

Natural exogenous surfactant products, regardless of their source, contain hydrophobic SPs and lipids. As heat-sterilized, nonpyrogenic suspensions, they are natural products containing the proteins that enhance surfactant distribution in human alveoli. Beractant is an augmented natural product. The addition of DPPC, tripalmitin, and palmitic acid brings the phospholipid content to roughly 90%. Therefore, beractant, as well as the other naturally derived surfactants, mimics endogenous surfactant, with proteins spreading and dispersing the phospholipid. The theoretical advantage of the natural surfactants appears to be a faster onset of action. The more recently marketed natural products, calfactant and poractant, contain higher concentrations of SP-B and natural surfactant phospholipids than does beractant.

A purely synthetic product, colfosceril, lacks a protein-containing matrix. Its surfactant matrix includes DPPC, cetyl alcohol, tyloxapol, and sodium chloride. Lucinactant belongs to a new generation of synthetic surfactants containing sinapultide, a 21-residue leucine-lysine peptide designed to mimic SP-B. Lucinactant is an isotonic aqueous suspension of the sinapultide peptide combined with the DPPC and palmitoyloleoyl phosphatidylglycerol phospholipids at a weight ratio of 3:1, as well as palmitic acid (15%). This engineered product may be more resistant to inactivation by meconium components, in addition to having the advantages of a synthetic product, including decreased risk of patients acquiring an infectious disease from the product and immunologic sensitization (because it is not derived from animals) and the potential to be produced in unlimited quantities while maintaining consistent drug quality.

Allogeneic cells may be used for progenitor cell isolation and subsequent transplantation. Most of the clinical manifestations of lung dysfunction arise from cell damage and impairment of the normal lung capacities. Major lung diseases include congenital lung hypoplasia; chronic lung disease of prematurity; and pulmonary emphysema. The enhancement of surfactant production is of interest for treating neonatal or adult RDS. Prevention of alveolar epithelial loss and inhibition of fibroblast proliferation is of interest for treatment of pulmonary fibrosis. Delivery of functional CFTR is of interest for treatment of cystic fibrosis. The lung homing properties of the cells also provide a means of delivering therapeutic agents to the lungs, e.g. to target the alveolus specifically for drug delivery during injuries such as ARDS and BPD.

Included in conditions of interest for treatment is bronchopulmonary dysplasia (BPD) is a chronic lung disease that occurs in very premature infants and is characterized by impaired alveologenesis. BPD may be defined as an impairment of alveolar formation, leading to long-term global reduction in alveolar number and gas-exchange surface area. BPD is considered to result from the impact of injury, including oxygen toxicity, barotrauma/volutrauma, and infection, on a very immature lung, which leads in turn to arrest of normal maturation, with possible variable susceptibility due to some gene polymorphisms.

Asthma is a pulmonary disease characterized by reversible airway obstruction, airway inflammation, and increased airway responsiveness to a variety of stimuli. Airway obstruction in asthma is due to a combination of factors that include spasm of airway smooth muscle, edema of airway mucosa, increased mucus secretion, cellular (especially eosinophilic and lymphocytic) infiltration of the airway walls, and injury and desquamation of the airway epithelium. Typically, asthmatics with active disease have hyperresponsive (hyperreactive) airways, manifest as an exaggerated bronchoconstrictor response to many different stimuli. The degree of hyperresponsiveness is closely linked to the extent of inflammation, and both correlate closely with the severity of the disease and the need for drugs. However, the cause of hyperresponsive airways is not known. Structural changes in the airways may contribute to it. Another possible cause of airway hyperresponsiveness is airway remodeling resulting in a small increase in airway thickness. Inflammatory disease of the airways is known to play a critical role, particularly in chronic asthma. Even in mild asthma, there is an inflammatory response involving infiltration, particularly with activated eosinophils and lymphocytes but also with neutrophils and mast cells; epithelial cell desquamation also occurs. Mast cells seem important in the acute response to inhaled allergens and perhaps to exercise but are less important than other cells in the pathogenesis of chronic inflammation. The number of eosinophils in peripheral blood and airway secretions correlates closely with the degree of bronchial hyperresponsiveness. In the USA, about 12 million persons have asthma. From 1982 to 1992, the prevalence of asthma increased from 34.7 to 49.4 per 1000. At the same time, the death rate increased 40%.

Emphysema is characterized by abnormal permanent enlargement of the airspaces distal to the terminal bronchioles with destruction of their walls and without obvious fibrosis. Destruction is defined as irregular enlargement of respiratory airspaces; the orderly appearance of the acinus and its components is disturbed and may be lost. Emphysema is classified according to the portion of the acinus (respiratory tissues distal to a single terminal bronchiole) affected by mild disease. Centrilobular emphysema (CLE) begins in the respiratory bronchiole and spreads peripherally. It is the most common form of emphysema in smokers and affects upper and posterior portions of the lungs more severely than the bases. Focal PAE often accompanies CLE in smokers and predominates at the bases. In emphysema, elastin fibers in the lung parenchyma are ruptured and frayed, and may result from elastic fibers digested by unopposed neutrophil elastase, which is normally opposed by $\alpha_1$-antitrypsin.

Genes may be introduced into the cells prior to culture or transplantation for a variety of purposes, e.g. prevent or reduce susceptibility to infection, replace genes having a loss of function mutation, in particular CFTR, etc. Alternatively, vectors are introduced that express antisense mRNA or ribozymes, thereby blocking expression of an undesired gene. Other methods of gene therapy are the introduction of drug resistance genes to enable normal progenitor cells to have an advantage and be subject to selective pressure, for example the multiple drug resistance gene (MDR), or anti-apoptosis genes, such as bcl-2. Various techniques known in the art may be used to transfect the target cells, e.g. electroporation, calcium precipitated DNA, fusion, transfection, lipofection and the like. The particular manner in which the DNA is introduced is not critical to the practice of the invention.

Many vectors useful for transferring exogenous genes into mammalian cells are available. The vectors may be episomal, e.g. plasmids, virus derived vectors such cytomegalovirus, adenovirus, etc., or may be integrated into the target cell genome, through homologous recombination or random integration, e.g. retrovirus derived vectors such MMLV, HIV-1, ALV, etc. For examples of progenitor and stem cell genetic alteration, see Svendsen et al. (1999) *Trends Neurosci.* 22(8):357-64; Krawetz at al. (1999) *Gene* 234(1):1-9; Pellegrini at al. *Med Biol Eng Comput.* 36(6):778-90; and Alison (1998) *Curr Opin Cell Biol.* 10(6):710-5.

Alternatively, the lung progenitors can be immortalized-disimmortalized (for example, see Kobayashi et al. (2000) *Science* 287:1258-1262. In such a procedure, an immortalizing genetic sequence, e.g. an oncogene, is introduced into the cell, in such a manner hat it can be readily removed, for example with a site specific recombinase such as the cre-lox system.

To prove that one has genetically modified progenitor cells, various techniques may be employed. The genome of the cells may be digested with restriction enzymes and used with or without DNA amplification. The polymerase chain reaction; gel electrophoresis; restriction analysis; Southern, Northern, and Western blots; sequencing; or the like, may all be employed. The cells may be grown under various conditions to ensure that the cells are capable of differentiation while maintaining the ability to express the introduced DNA. Various tests in vitro and in vivo may be employed to ensure that the pluripotent capability of the cells has been maintained.

The cells may be administered in any physiologically acceptable medium, normally intravascularly, including intravenous, e.g. through the lung portal vein; intrasplenic, etc. although they may also be introduced into other convenient sites, where the cells may find an appropriate site for regeneration and differentiation. Usually, at least $1 \times 10^3$/Kg cells will be administered, more usually at least about $1 \times 10^4$/Kg, preferably $1 \times 10^6$/Kg or more. The cells may be introduced by injection, catheter, or the like.

Pathogens

The animal models and cells of the invention find use in investigating the effect of pulmonary pathogens, for screening candidate agents that interact with such pathogens, to investigate pathogen induced alteration of lung function, and the like. Many pulmonary pathogens are well-known. Such pathogens include a variety of respiratory viruses, including, for example, influenza viruses, parainfluenza viruses, rhinoviruses, adenoviruses, respiratory syncytial virus, etc.

Bacterial pathogens of the lungs are also well-known. For example, pneumonia is an acute infection of lung parenchyma including alveolar spaces and interstitial tissue; it ranks sixth among all disease categories as a cause of death and is the most common lethal nosocomial (hospital-acquired) infection. Bacteria are the most common cause of pneumonia in adults, including *Streptococcus pneumoniae; Staphylococcus aureus, Haemophilus influenzae, Chlamydia pneumoniae, C. psittaci, C. trachomatis, Moraxella (Branhamella) catarrhalis, Legionella pneumophila, Klebsiella pneumoniae*, and other gram-negative bacilli. *Mycoplasma pneumoniae*, a bacteria-like organism, is particularly common in older children and young adults, typically in the spring. Among other agents are higher bacteria including *Nocardia* and *Actinomyces* sp; mycobacteria, including *Mycobacterium tuberculosis* and atypical strains (primarily *M. kansasii* and *M. avium-intracellulare*); fungi, including *Histoplasma capsulatum, Coccidioides immitis, Blastomyces dermatitidis, Cryptococcus neoformans, Aspergillus fumigatus,* and *Pneumocystis carinii*; and rickettsiae, primarily *Coxiella burnetii* (Q fever).

An infection of particular note is tuberculosis, which refers to disease caused by *Mycobacterium tuberculosis*, with related diseases attributable to *M. bovis*, or *M. africanum*. *Mycobacterium avium* intracellularae is another important *mycobacterium*, which especially affects patients with bronchiectasis.

Human TB occurs almost exclusively from inhalation of organisms dispersed as droplet nuclei from a person with pulmonary TB whose sputum smear is positive. *M. tuberculosis* may float in the air for several hours, thus increasing the chance of spread. Spread can occur in mycobacteriology laboratories and autopsy rooms, in part because the hydrophobic nature of the organism facilitates aerosolization. Fomites appear to play no role in their spread. The stages of TB are primary or initial infection, latent or dormant infection, and recrudescent or adult-type TB. Ninety to 95% of primary TB infections go unrecognized, producing only a positive tuberculin skin test and a latent or dormant infection. Primary TB may become active at any age, producing clinical TB in any organ, most often the apical area of the lung but also the kidney, long bones, vertebrae, lymph nodes, and other sites. Often, activation occurs within 1 to 2 yr of initial infection, but may be delayed years or decades and activate after onset of diabetes mellitus, during periods of stress, after treatment with corticosteroids or other immunosuppressants, in adolescence, or in later life (>70 yr of age), but especially after HIV infection.

Expression Assays

Of interest is the examination of gene expression in lung progenitor cells. The expressed set of genes may be compared with a variety of cells of interest, e.g. adult lung progenitor cells, stem cells, hematopoietic cells, etc., as known in the art. For example, one could perform experiments to determine the genes that are regulated during development.

Any suitable qualitative or quantitative methods known in the art for detecting specific mRNAs can be used. mRNA can be detected by, for example, hybridization to a microarray, in situ hybridization in tissue sections, by reverse transcriptase-PCR, or in Northern blots containing poly A$^+$ mRNA. One of skill in the art can readily use these methods to determine differences in the size or amount of mRNA transcripts between two samples. For example, the level of particular mRNAs in progenitor cells is compared with the expression of the mRNAs in a reference sample, e.g. lungs, or other differentiated cells.

Any suitable method for detecting and comparing mRNA expression levels in a sample can be used in connection with the methods of the invention. For example, mRNA expression levels in a sample can be determined by generation of a library of expressed sequence tags (ESTs) from a sample. Enumeration of the relative representation of ESTs within the library can be used to approximate the relative representation of a gene transcript within the starting sample. The results of EST analysis of a test sample can then be compared to EST analysis of a reference sample to determine the relative expression levels of a selected polynucleotide, particularly a polynucleotide corresponding to one or more of the differentially expressed genes described herein.

Alternatively, gene expression in a test sample can be performed using serial analysis of gene expression (SAGE) methodology (Velculescu et al., Science (1995) 270:484). SAGE involves the isolation of short unique sequence tags from a specific location within each transcript. The sequence tags are concatenated, cloned, and sequenced. The frequency of particular transcripts within the starting sample is reflected by the number of times the associated sequence tag is encountered with the sequence population.

Gene expression in a test sample can also be analyzed using differential display (DD) methodology. In DD, fragments defined by specific polynucleotide sequences (or restriction enzyme sites) are used as unique identifiers of genes, coupled with information about fragment length or fragment location within the expressed gene. The relative representation of an expressed gene with in a sample can then be estimated based on the relative representation of the fragment associated with that gene within the pool of all possible fragments. Methods and compositions for carrying out DD are well known in the art, see, e.g., U.S. Pat. No. 5,776,683; and U.S. Pat. No. 5,807,680.

Alternatively, gene expression in a sample using hybridization analysis, which is based on the specificity of nucleotide interactions. Oligonucleotides or cDNA can be used to selectively identify or capture DNA or RNA of specific sequence composition, and the amount of RNA or cDNA hybridized to a known capture sequence determined qualitatively or quantitatively, to provide information about the relative representation of a particular message within the pool of cellular messages in a sample. Hybridization analysis can be designed to allow for concurrent screening of the relative expression of hundreds to thousands of genes by using, for example, array-based technologies having high density formats, including filters, microscope slides, or microchips, or solution-based technologies that use spectroscopic analysis (e.g., mass spectrometry). One exemplary use of arrays in the diagnostic methods of the invention is described below in more detail.

Hybridization to arrays may be performed, where the arrays can be produced according to any suitable methods known in the art. For example, methods of producing large arrays of oligonucleotides are described in U.S. Pat. No. 5,134,854, and U.S. Pat. No. 5,445,934 using light-directed synthesis techniques. Using a computer controlled system, a heterogeneous array of monomers is converted, through simultaneous coupling at a number of reaction sites, into a heterogeneous array of polymers. Alternatively, microarrays are generated by deposition of pre-synthesized oligonucleotides onto a solid substrate, for example as described in PCT published application no. WO 95/35505.

Methods for collection of data from hybridization of samples with an arrays are also well known in the art. For example, the polynucleotides of the cell samples can be generated using a detectable fluorescent label, and hybridization of the polynucleotides in the samples detected by scanning the microarrays for the presence of the detectable label. Methods and devices for detecting fluorescently marked targets on devices are known in the art. Generally, such detection devices include a microscope and light source for directing light at a substrate. A photon counter detects fluorescence from the substrate, while an x-y translation stage varies the location of the substrate. A confocal detection device that can be used in the subject methods is described in U.S. Pat. No. 5,631,734. A scanning laser microscope is described in Shalon et al., Genome Res. (1996) 6:639. A scan, using the appropriate excitation line, is performed for each fluorophore used. The digital images generated from the scan are then combined for subsequent analysis. For any particular array element, the ratio of the fluorescent signal from one sample is compared to the fluorescent signal from another sample, and the relative signal intensity determined.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e. data deviating from a predetermined statistical distribution, and calculating the relative binding affinity of the targets from the remaining data. The resulting data can be displayed as an image with the intensity in each region varying according to the binding affinity between targets and probes.

Pattern matching can be performed manually, or can be performed using a computer program. Methods for preparation of substrate matrices (e.g., arrays), design of oligonucleotides for use with such matrices, labeling of probes, hybridization conditions, scanning of hybridized matrices, and analysis of patterns generated, including comparison analysis, are described in, for example, U.S. Pat. No. 5,800,992.

In another screening method, the test sample is assayed at the protein level. Diagnosis can be accomplished using any of a number of methods to determine the absence or presence or altered amounts of a differentially expressed polypeptide in the test sample. For example, detection can utilize staining of cells or histological sections (e.g., from a biopsy sample) with labeled antibodies, performed in accordance with conventional methods. Cells can be permeabilized to stain cytoplasmic molecules. In general, antibodies that specifically bind a differentially expressed polypeptide of the invention are added to a sample, and incubated for a period of time sufficient to allow binding to the epitope, usually at least about 10 minutes. The antibody can be detectably labeled for direct detection (e.g., using radioisotopes, enzymes, fluorescers, chemiluminescers, and the like), or can be used in conjunction with a second stage antibody or reagent to detect binding (e.g., biotin with horseradish peroxidase-conjugated avidin, a secondary antibody conjugated to a fluorescent compound, e.g. fluorescein, rhodamine, Texas red, etc.). The absence or presence of antibody binding can be determined by various methods, including flow cytometry of dissociated cells, microscopy, radiography, scintillation counting, etc. Any suitable alternative methods of qualitative or quantitative detection of levels or amounts of differentially expressed polypeptide can be used, for example ELISA, western blot, immunoprecipitation, radioimmunoassay, etc.

Screening Assays

The subject cells are useful for in vitro assays and screening to detect agents that affect lung progenitor cells and differentiated cells that are the progeny of lung progenitor cells. A wide variety of assays may be used for this purpose, including toxicology testing, immunoassays for protein binding; determination of cell growth, differentiation and functional activity; production of hormones; and the like.

In screening assays for biologically active agents, viruses, etc. the subject cells, usually a culture comprising the subject cells, is contacted with the agent of interest, and the effect of the agent assessed by monitoring output parameters, such as expression of markers, cell viability, and the like. The cells may be freshly isolated, cultured, genetically altered as described above, or the like. The cells may be environmentally induced variants of clonal cultures: e.g. split into independent cultures and grown under distinct conditions, for example with or without virus; in the presence or absence of other cytokines or combinations thereof. The manner in which cells respond to an agent, particularly a pharmacologic agent, including the timing of responses, is an important reflection of the physiologic state of the cell.

Parameters are quantifiable components of cells, particularly components that can be accurately measured, desirably in a high throughput system. A parameter can be any cell component or cell product including cell surface determinant, receptor, protein or conformational or posttranslational modification thereof, lipid, carbohydrate, organic or inorganic molecule, nucleic acid, e.g. mRNA, DNA, etc. or a portion derived from such a cell component or combinations thereof. While most parameters will provide a quantitative readout, in some instances a semi-quantitative or qualitative result will be acceptable. Readouts may include a single determined value, or may include mean, median value or the variance, etc. Characteristically a range of parameter readout values will be obtained for each parameter from a multiplicity of the same assays. Variability is expected and a range of values for each of the set of test parameters will be obtained using standard statistical methods with a common statistical method used to provide single values.

Agents of interest for screening include known and unknown compounds that encompass numerous chemical classes, primarily organic molecules, which may include organometallic molecules, inorganic molecules, genetic sequences, etc. An important aspect of the invention is to evaluate candidate drugs, including toxicity testing; and the like.

In addition to complex biological agents, such as viruses, candidate agents include organic molecules comprising functional groups necessary for structural interactions, particularly hydrogen bonding, and typically include at least an amine, carbonyl, hydroxyl or carboxyl group, frequently at least two of the functional chemical groups. The candidate agents often comprise cyclical carbon or heterocyclic structures and/or aromatic or polyaromatic structures substituted with one or more of the above functional groups. Candidate agents are also found among biomolecules, including peptides, polynucleotides, saccharides, fatty acids, steroids, purines, pyrimidines, derivatives, structural analogs or combinations thereof.

Included are pharmacologically active drugs, genetically active molecules, etc. Compounds of interest include chemotherapeutic agents, hormones or hormone antagonists, etc. Exemplary of pharmaceutical agents suitable for this invention are those described in, "The Pharmacological Basis of Therapeutics," Goodman and Gilman, McGraw-Hill, New York, N.Y., (1996), Ninth edition, under the sections: Water, Salts and Ions; Drugs Affecting Renal Function and Electrolyte Metabolism; Drugs Affecting Gastrointestinal Function; Chemotherapy of Microbial Diseases; Chemotherapy of Neoplastic Diseases; Drugs Acting on Blood-Forming organs; Hormones and Hormone Antagonists; Vitamins, Dermatology; and Toxicology, all incorporated herein by reference. Also included are toxins, and biological and chemical warfare agents, for example see Somani, S. M. (Ed.), "Chemical Warfare Agents," Academic Press, New York, 1992).

Test compounds include all of the classes of molecules described above, and may further comprise samples of unknown content. Of interest are complex mixtures of naturally occurring compounds derived from natural sources such as plants. While many samples will comprise compounds in solution, solid samples that can be dissolved in a suitable solvent may also be assayed. Samples of interest include environmental samples, e.g. ground water, sea water, mining waste, etc.; biological samples, e.g. lysates prepared from crops, tissue samples, etc.; manufacturing samples, e.g. time course during preparation of pharmaceuticals; as well as libraries of compounds prepared for analysis; and the like. Samples of interest include compounds being assessed for potential therapeutic value, i.e. drug candidates.

The term samples also includes the fluids described above to which additional components have been added, for example components that affect the ionic strength, pH, total protein concentration, etc. In addition, the samples may be treated to achieve at least partial fractionation or concentration. Biological samples may be stored if care is taken to reduce degradation of the compound, e.g. under nitrogen, frozen, or a combination thereof. The volume of sample used is sufficient to allow for measurable detection, usually from about 0.1:1 to 1 ml of a biological sample is sufficient.

Compounds, including candidate agents, are obtained from a wide variety of sources including libraries of synthetic or natural compounds. For example, numerous means are available for random and directed synthesis of a wide variety of organic compounds, including biomolecules, including expression of randomized oligonucleotides and oligopeptides. Alternatively, libraries of natural compounds in the form of bacterial, fungal, plant and animal extracts are available or readily produced. Additionally, natural or synthetically produced libraries and compounds are readily modified through conventional chemical, physical and biochemical means, and may be used to produce combinatorial libraries. Known pharmacological agents may be subjected to directed or random chemical modifications, such as acylation, alkylation, esterification, amidification, etc. to produce structural analogs.

Agents are screened for biological activity by adding the agent to at least one and usually a plurality of cell samples, usually in conjunction with cells lacking the agent. The change in parameters in response to the agent is measured, and the result evaluated by comparison to reference cultures, e.g. in the presence and absence of the agent, obtained with other agents, etc.

The agents are conveniently added in solution, or readily soluble form, to the medium of cells in culture. The agents may be added in a flow-through system, as a stream, intermittent or continuous, or alternatively, adding a bolus of the compound, singly or incrementally, to an otherwise static solution. In a flow-through system, two fluids are used, where one is a physiologically neutral solution, and the other is the same solution with the test compound added. The first fluid is passed over the cells, followed by the second. In a single solution method, a bolus of the test compound is added to the volume of medium surrounding the cells. The overall concentrations of the components of the culture medium should not change significantly with the addition of the bolus, or between the two solutions in a flow through method.

Preferred agent formulations do not include additional components, such as preservatives, that may have a significant effect on the overall formulation. Thus preferred formulations consist essentially of a biologically active compound and a physiologically acceptable carrier, e.g. water, ethanol, DMSO, etc. However, if a compound is liquid without a solvent, the formulation may consist essentially of the compound itself.

A plurality of assays may be run in parallel with different agent concentrations to obtain a differential response to the various concentrations. As known in the art, determining the effective concentration of an agent typically uses a range of concentrations resulting from 1:10, or other log scale, dilutions. The concentrations may be further refined with a second series of dilutions, if necessary. Typically, one of these concentrations serves as a negative control, i.e. at zero concentration or below the level of detection of the agent or at or below the concentration of agent that does not give a detectable change in the phenotype.

Various methods can be utilized for quantifying the presence of the selected markers. For measuring the amount of a molecule that is present, a convenient method is to label a molecule with a detectable moiety, which may be fluorescent, luminescent, radioactive, enzymatically active, etc., particularly a molecule specific for binding to the parameter with high affinity Fluorescent moieties are readily available for labeling virtually any biomolecule, structure, or cell type. Immunofluorescent moieties can be directed to bind not only to specific proteins but also specific conformations, cleavage products, or site modifications like phosphorylation. Individual peptides and proteins can be engineered to autofluoresce, e.g. by expressing them as green fluorescent protein chimeras inside cells (for a review see Jones et al. (1999) *Trends Biotechnol.* 17(12):477-81). Thus, antibodies can be genetically modified to provide a fluorescent dye as part of their structure. Depending upon the label chosen, parameters may be measured using other than fluorescent labels, using such immunoassay techniques as radioimmunoassay (RIA) or enzyme linked immunosorbance assay (ELISA), homogeneous enzyme immunoassays, and related non-enzymatic techniques. The quantitation of nucleic acids, especially messenger RNAs, is also of interest as a parameter. These can be measured by hybridization techniques that depend on the sequence of nucleic acid nucleotides. Techniques include polymerase chain reaction methods as well as gene array techniques. See Current Protocols in Molecular Biology, Ausubel et al., eds, John Wiley & Sons, New York, N.Y., 2000; Freeman et al. (1999) *Biotechniques* 26(1):112-225; Kawamoto et al. (1999) *Genome Res* 9(12):1305-12; and Chen et al. (1998) *Genomics* 51(3):313-24, for examples.

EXPERIMENTAL

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

All publications and patent applications cited in this specification are herein incorporated by reference as if each individual publication or patent application were specifically and individually indicated to be incorporated by reference.

The citation of any publication is for its disclosure prior to the filing date and should not be construed as an admission that the present invention is not entitled to antedate such publication by virtue of prior invention.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

Example 1

Identification of a Candidate Lung Alveolar Endothelial Progenitor (Abbreviations) EPC=endothelial progenitor cell, HSC=Hematopoietic stem cell, Sca-1=Stem cell antigen-1, KDR=VEGFR-2, vascular endothelial growth factor receptor, type 2.

Despite its apparent simple structure, the alveoli of the lung are difficult to regenerate after injury. The cellular composition of alveoli include Type I and II epithelial cells; specialized endothelial cells that form the other half of the air-blood interface; and other mesenchymal elements such as myofibroblasts. The lung also includes immune elements such as macrophages and lymphocytes which continually transit through the lung. The mechanisms of repair and maintenance of adult alveoli are not understood. It is hypothesized that these mechanisms of repair overlap with alveolar development, which is better understood. Alveolization and microvascular maturation, which represent full differentiation of alveolar epithelial and endothelial tissue, begins at gestational age week 36 in humans and continues through the second post-natal year.

In mice, alveolar maturation takes place on postnatal days 0 through 40. Alveolar epithelial and endothelial development occur simultaneously and involve co-regulation and induction. Alveolar epithelial development is characterized by a pattern of proliferation of cuboidal immature cells that as a population eventually differentiate into the surfactant secreting Type II cells and the flat gas-exchange Type I cells. It is thought that a multipotent lung epithelial progenitor gives rise to the two mature alveolar epithelial cell types. Alveolar endothelial development (microvascular maturation) follows a pattern whereby a bilayer of capillaries surrounding each alveolus is eventually remodeled into a monolayer, so that adjacent alveoli share one capillary bed, a more efficient arrangement for gas exchange. It is possible that the lung repairs itself after injury from endogenous stem cells, cells that at the single cell level can give rise to clonal progeny that includes stem cells by self-renewal, and mature progeny by differentiation.

In this study we have pursued the prospective isolation of the several types of mouse lung progenitor/stem cells by transplantation of phenotypically marked candidate populations into recipients. In order to create niche space permissive to the establishment and expansion of primitive lung cells, adult recipients underwent lung injury by exposure to lethal radiation. Radiation induced lung injury is well characterized in humans and animals. In rodents, endothelial injury can be detected in serum (increasing levels of circulating ICAM) five hours after high dose radiation. Endothelial injury becomes apparent histologically before epithelial injury, and both cell types manifest injury by one week after radiation. Donors in our study were mice at the age of five weeks, an age at which active alveolar development is occurring. By transplanting marked putative lung progenitor or stem cells into recipients with injured lungs, we observed that a phenotypically defined subset of cells from dissociated lung)(CD45$^-$Sca-1$^+$Notch1$^{-/lo}$ contributed to regeneration of intact alveolar capillary networks that expand over time.

Materials and Methods

Animals were handled in accordance with institutional guidelines and with the approved internal animal protocol.

Lung Dissociation:

Single cell lung suspensions were generated using a modification of methods previously described by Corti et al. Lungs were dissociated using a combination of enzymatic and mechanical dispersion. The lungs were infused intratracheally with a solution of 1.5 mL of Saline/5 mM $CaCl_2$/Dispase using Dispase (Worthington) at a concentration of 2.4 U per mL. A plug of 0.5 mL of liquid 1% low-melt agarose (Sigma) in PBS was infused into the lungs, which were then packed with ice to solidify the low-melt agarose. The lungs were incubated at room temperature for 45-60 minutes, then the lungs were teased apart with forceps, gently pipetted to generate a nearly homogenous mixture, and then serially filtered through 100 µm and 40 µm nylon mesh filters. The red cells were lysed with urea-based lysis buffer and then washed once with media.

Transgenic Mice:

Five week old transgenic mice that constitutively expressed reporters were used as lung cell donors. For the in vivo homing experiments, FVB mice with an insertion of firefly luciferase under β-actin promoter control were used as the lung or liver cell donors. Wildtype FVB animals were the recipients in these experiments. For experiments using GFP donors, C57BL6 mice with an insertion of enhanced-GFP under β-actin promoter control were used. The recipients were on the C57BL6 background.

FACS.

FACS analysis of dissociated lung cells was performed by staining with monoclonal antibodies against PECAM (BD Biosciences), CD45 (eBiosciences), Sca-1 (eBiosciences), the extracellular component of Notch1 (NeoMarkers), CD133 (eBiosciences), KDR (eBiosciences), and CD34 (eBiosciences). A modified dual laser flow cytometer LSRScan (BD Immunocytometry Systems) was used for data acquisition, and FlowJo (Tree Star, Inc.) was used to analyze the data. Preparative FACS sorting was performed by subjecting the lung single cell suspension from five to ten pairs of juvenile lungs to staining with monoclonal antibodies against Sca-1, Notch1, and CD45. Viable cells were selected for by their exclusion of propidium iodide. All donor cells are GFP$^+$. The cells were sorted on a modified dual laser FACSVantage system (BD Immunocytometry Systems).

Transplantation:

Recipient mice underwent preparation for transplant with myeloablative radiation eight to twelve hours prior to the infusion of lung derived and hematopoietic cells. The radiation was delivered in split doses at 950cGy for C57BL6 strain and 800cGy for FVB. GFP$^+$ lung cells were prepared as above, and unmarked HSCs (Lineage$^-$, Thy1.1$^{lo}$, Sca-1$^+$, c-Kit$^+$) were prepared according to previously published protocols. The GFP$^+$ lung cells were mixed with 1500 unmarked HSCs and injected intravenously into the tail vein.

Engraftment and Differentiation:

The presence of donor-lung cells was assessed by immunofluorescence microscopy of histologic sections of recipient lung. Mice were first anesthetized and the right ventricle (RV) was then perfused with 10 mL of 10 mM EDTA in PBS, and then 10 mL of 2% formaldehyde+0.5% methanol in PBS. The lungs were inflated with 0.5 mL of the fixative mixture and held in an inflated state for 15 minutes, followed by dissection and further incubation in fixative solution at room temperature for an additional 100 minutes. Lungs were then washed with 30% sucrose, and left in 30% sucrose overnight. The fixed lungs were then frozen in OCT and stored at −80° C. until cryosectioning. 10 µm and 40 µm thick sections were cut. The slides were allowed to air-dry, post-fixed with ice-cold methanol for 3 minutes, washed in PBS and then blocked and stained (Avidin/Biotin block—Invitrogen/Molecular Probes, anti-CD45—eBiosciences, Goat anti-Rat IgG Alexa 350—Invitrogen/Molecular Probes, anti-T1α/8.1.1, anti-PECAM-Biotin—eBiosciences, Streptavidin-Alexa594, Goat anti-Hamster Alexa 594 or 670, Goat anti-rabbit Alexa 594 or 670—Molecular Probes/Invitrogen). Native GFP fluorescence was detected in the FITC channel. A Nikon inverted microscope was used for standard fluorescence microscopy, and a LEICA SP2 microscope was used for confocal microscopy. For confocal microscopy, emittance spectra were manually set to eliminate overlap between fluorochromes used on the same section.

Results

Figure 6:
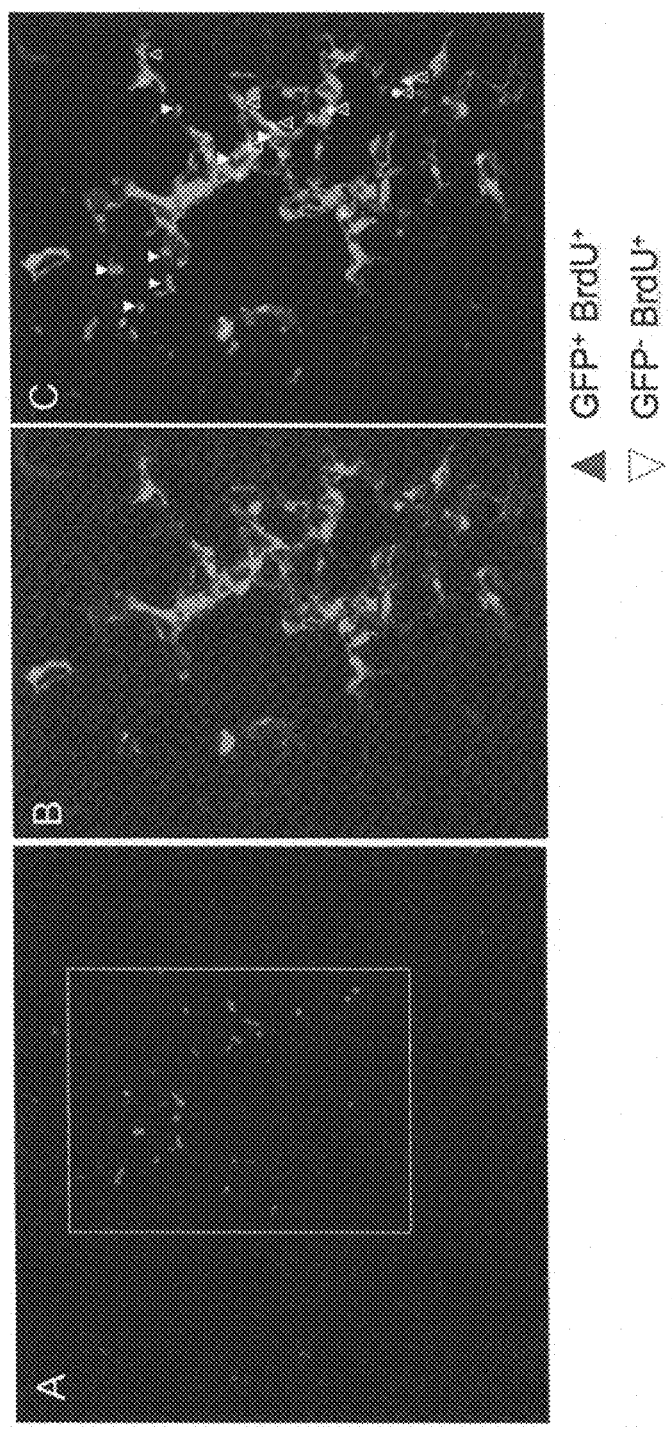
FIG. 6. Segregation of lung cells by flow cytometry. Dissociated lung cells were analyzed by FACS for viability and segregation into distinct populations based staining for non-epithelial lineage markers. A. Analysis for viability with propidium iodide showed 75-88% viability. B. Viable cells were stained with CD45 and PECAM, generating four fractions, labeled a-d. 20-25% of the viable cells CD45− PECAM−C.

Dissociation of lung cells and separation into distinct populations. Five week old mice were used as the source for lung progenitor cells. In mouse lung development, alveolar microvascular maturation continues for six weeks after birth, and therefore, four-five week old mice likely contain lung progenitor cells. Established methods were adapted to prepare single cell suspensions of viable dissociated lung. Lungs were infused intratracheally with a dispase solution, allowed to enzymatically digest in situ, and then mechanically disrupted and filtered. Each pair of lungs yielded 25-30 million cells, with ~80% viability as demonstrated by exclusion of propidium iodide when assessed by FACS analysis (see FIG. 6).

When CD45 and CD31 (PECAM) were applied to FACS analysis of dissociated lung, four distinct populations were defined. The single-positive CD31 fraction contains endothelial cells, and the single-positive CD45 fraction contains blood cells. Co-expression of CD31 on white blood cells is essential for migration across endothelial barriers. Therefore, the CD45$^+$CD31$^+$ double-positive cells likely include a mixture of macrophages and other leukocytes which migrated into the extravascular spaces of the lung (intra-alveolar or interstitial). The remaining CD45$^-$CD31$^-$ double-negative fraction encompasses the airspace lumen and interstitial cells that are not leukocytes or endothelial cells. This population includes epithelial cells, secretory cells, neuroendocrine cells, and fibroblasts. We chose to focus on the CD45$^-$ population because it is most likely enriched for epithelial and endothelial progenitor/stem cells. Since CD31 may be expressed by more primitive endothelial cells, it was not used as a negative selection marker so as not to exclude EPCs.

CD45⁻ lung cells specifically home to and durably engraft in injured recipient lungs in vivo. FIG. 2A shows the schematic of our in vivo experiments used to identify putative progenitor lung populations. Marked donor lungs were fractionated into defined subsets and transplanted into radiation-injured recipients. Concurrently, unlabeled HSCs were used to rescue hematopoiesis in the irradiated recipients. For histologic analysis of engraftment into lung, tissues were harvested from animals four and eight weeks after cell transplantation.

To study homing of dissociated lung cells in vivo, transgenic mice that express the bioluminescent reporter firefly luciferase driven by a β-Actin promoter were used as lung donors. Because we wished only to exclude blood lineage cells without excluding any lung lineage, whether they were epithelial, endothelial or other, the bulk population was divided into CD45 positive and negative fractions. In recipients that received no radiation, transfer of luciferase-marked donor lung cells showed no bioluminescent signal in vivo. Conversely, only irradiated recipients showed homing of donor cells to lung. The CD45⁺ fraction of lung cells did not traffic to lung in sufficient numbers to be detectable, and the bioluminescent signal was not seen (FIG. 1B). In contrast, CD45⁻ cells trafficked specifically to injured lung, indicating specificity in their homing from blood to lung. Furthermore, animals that received unfractionated lung cells with an equivalent dose of CD45⁻ cells had the same photon counts in the chest as the animals that received only CD45⁻ cells, showing that the transplanted CD45⁻ cells account for all of the bioluminescent signal. To determine whether or not recipients lungs were simply non-specifically trapping dissociated cell populations, the CD45⁻ fraction of dissociated liver was transplanted into irradiated animals and showed that there was little signal in the chest. As a further control, CD45⁺ lung cells, CD45⁻ lung cells and liver cells from transgenic donors were imaged in separate wells in a 96 well plate and shown to produce equivalent photons per cell.

The CD45⁻ lung cells durably engrafted in recipient lung as evidenced by the persistence of bioluminescent signal in the 10 lethally irradiated recipients that received $10^6$ CD45⁻ luciferase-marked lung cells plus $10^6$ unmarked bone marrow cells each. These recipients were serially imaged over 35 days. FIG. 1C shows a representative animal visualized at 3 hours, 1, 5, 7 and 35 days post-infusion. The bioluminescent photon counts remained stable through this period. In later experiments, animals were rescued with purified HSCs, and not unfractionated bone marrow. Purified HSCs do not engraft as non-blood cells into lung, and the capacity of non-HSC cells contained in unfractionated bone marrow to engraft into lung is uncertain.

Preparative sorting of dissociated lung cells by stem cell surface markers. To further characterize the phenotype of lungs cells that engrafted into irradiated recipients, the CD45⁻ population was further fractionated using established stem cell surface markers, Sca-1, Notch1, c-Kit and Thy-1.1. Candidate stem cell markers were screened by the in vivo engraftment assay outlined in FIG. 1A. In order to visualize the engrafting cells by histology, lung donors were transgenic mice that express GFP rather than luciferase (driven by a β-Actin promoter). Multiparameter FACS was employed to define single- and double-positive populations using antibodies against the candidate markers in combinations of two antibody stains per sort. Single- and double-positive populations and the remaining double-negative populations were transplanted into separate experimental groups. After the initial screen, Sca-1 and Notch1 were chosen for further study because only these markers delineated cells that showed engraftment into recipient lungs. Sca-1 has been identified as an important molecule to mark mouse HSC and is also known to be expressed in lung endothelium. Notch1 has been described as an important signaling molecule in maintaining the undifferentiated fate of stem cells in blood and in other organs.

FIG. 2A shows the staining of the CD45⁻ fraction of dissociated lung with Sca-1 and Notch-1. Five phenotypically distinct populations were delineated by Sca-1 versus Notch1 and have been labeled populations a through e as follows: a=Sca-1⁻Notch1⁺, b=Sca-1$^{lo}$ Notch1⁺, c=Sca-1⁺Notch1⁺, d=Sca-1⁻Notch1$^{-/lo}$, e=Sca-1⁺Notch1$^{-/lo}$. Each of these GFP-marked populations was co-transplanted with unmarked HSC into irradiated mice. FIG. 2B shows the FACS profile of CD31 (PECAM) vs. Sca-1: >98% of the CD31+ cells are Sca-1+. As shown in FIG. 2C, there were significantly more CD31⁺ cells in the Sca-1⁺Notch1⁺ (86%) versus the Sca-1⁺Notch1$^{-/lo}$ population (3.8%). If any lung endothelial cell marked by CD31 is capable of engrafting into lungs then we would expect that the Sca-1⁺Notch⁺ population, which is significantly more enriched for PECAM⁺ cells, to show superior engraftment into recipient lung. Rather, the Sca-1⁺Notch1$^{-/lo}$ cells gave the significant positive readout suggesting that the endothelial clusters were not simply derived from mature endothelial cells.

Figure 3:
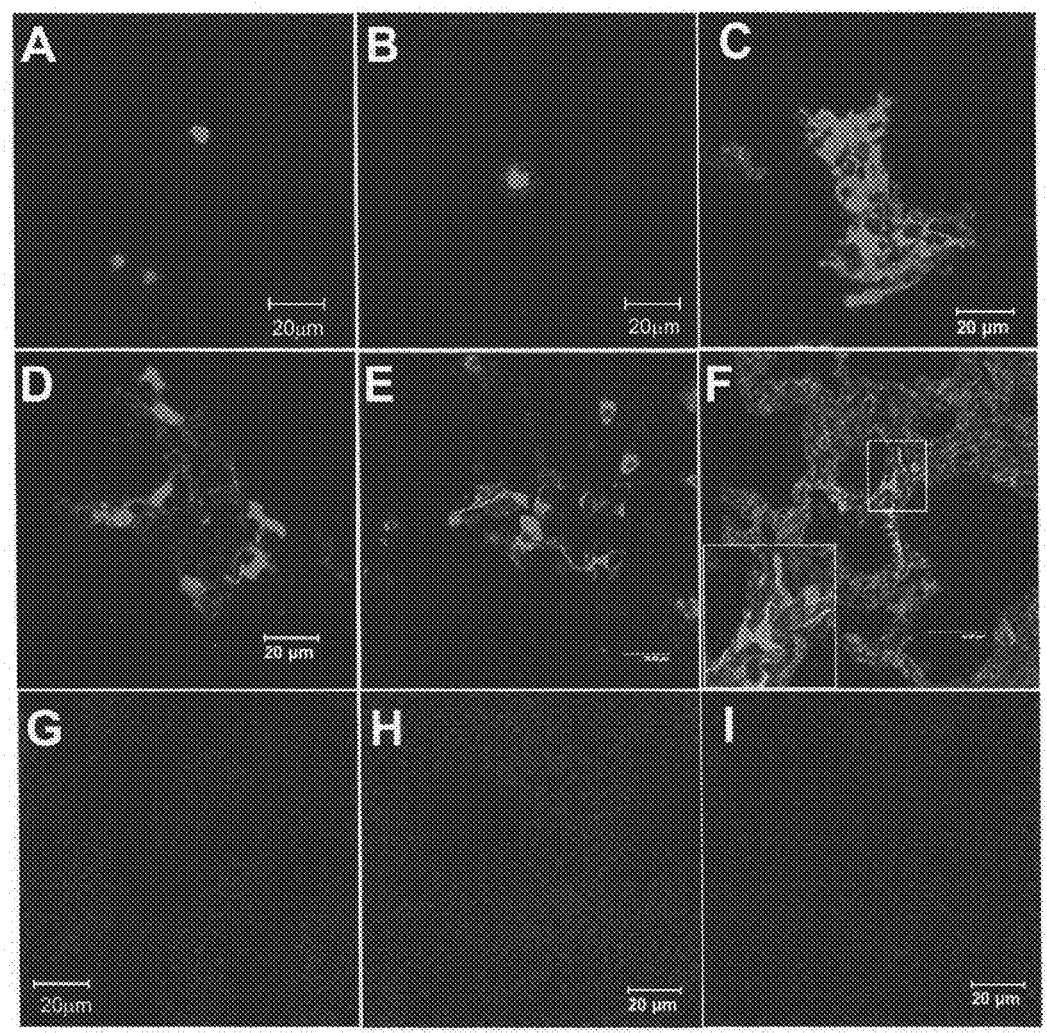
FIG. 3. Only $CD45^-$Sca-1$^+$Notch1$^{-/lo}$ lung cells (population E) engraft and expand into clusters in injured recipient lungs in vivo with morphological features of alveolar capillary endothelial cells. Panels A-D and G-I Fluorescence microscopy of native GFP fluorescence. A) Lung of recipient transplanted with lung-derived CD45$^+$ donor cells. B) Lung of recipient transplanted with lung-derived CD45$^-$ Sca-1$^-$Notch1$^-$ cells (FIG. 2A, population D). C,D) Lung of recipient transplanted with lung-derived CD45$^-$Sca-1$^+$ Notch1$^{-/lo}$ fraction (FIG. 2A, population E) showing clusters of cells with capillary endothelial morphology. E,F) 1 µm optical confocal sections of lung of mice transplanted with CD45$^-$ Sca-1$^+$Notch1$^{-/lo}$ cells. Panel E shows that GFP$^+$ cells do not co-localize with CD45 (leukocyte, blue) or with SP-C (Type II AEC, red). Panel F demonstrates that the cytoplasmic GFP is bounded by the cell surface marker PECAM (blue), and not immediately by the Type I AEC marker, T1α. G-I) overexposures of gut (G), liver (H) and brain (I), from the same recipient that show no GFP+ cells. AEC=alveolar epithelial cell. SP-C=Surfactant Protein C.

Only the Sca-1⁺Notch1$^{-/lo}$ population (population e) engrafted as cells of lung lineage. Although donor-derived GFP⁺ cells from populations a-d could be identified within recipient lung, they could be identified only as single CD45⁺ cells. (FIG. 3, panel B, CD45 staining not shown). This pattern of single GFP⁺ cells was similar to the pattern in control animals that received the CD45⁺ fraction of donor lung, which suggests that these cells were of hematopoietic lineage that contaminated the sorted fractions (FIG. 3, panel A).

CD45⁻Sca-1⁺Notch1$^{-/lo}$ lung progenitor cells (population e) engraft into recipient lung and form clusters of alveolar capillary endothelial cells. In contrast to populations a-d, the Sca-1⁺Notch1$^{-/lo}$ cells (population e) showed engraftment of GFP⁺ cells that expanded to form clusters (Table 1, FIG. 3, panels C, D). At four weeks post-transplant clusters appeared to be relatively uniform in size and cell number (60-100 cells/cluster), and they resembled the morphology of capillary networks surrounding alveoli. Confocal immunofluorescence microscopy was used to characterize the differentiated phenotype of engrafted GFP⁺ lung progenitor cells. The GFP⁺ cells (green) did not colocalize with CD45⁺ leukocytes (blue), nor with surfactant protein C-expressing type II alveolar epithelial cells (red) (FIG. 3, panel E). Rather, the cytoplasmic GFP signal (green) was immediately bounded by endothelial surface marker PECAM staining (blue) and never by the type I alveolar epithelial surface marker T1α/8.1.1 staining (red) (FIG. 3, panel F). T1α is a recognized marker of type I alveolar epithelial cells [31]. We conclude from these studies that the Sca-1⁺Notch1$^{-/lo}$ population is enriched for EPCs which engraft and expand into clusters of alveolar capillary cells. Other organs including gut, liver and brain were examined for the presence of GFP⁺ cells, and none were observed (FIG. 3, panels G-I).

Figure 4:
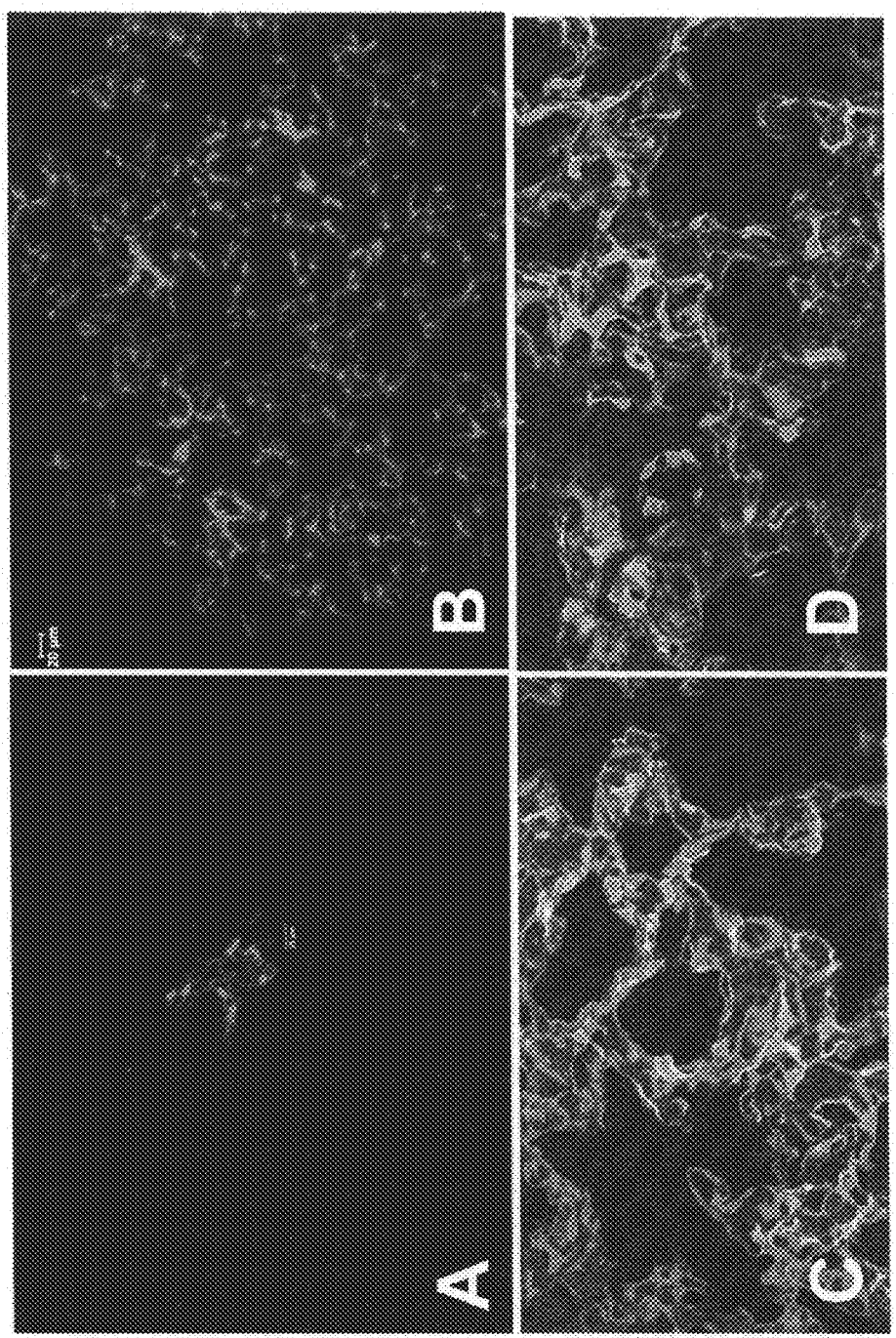
FIG. 4. Endothelial clusters expand with time. A) Cluster of donor-derived endothelial cells at four weeks post-transplant (Same cluster as FIG. 3, Panel D, but reduced to same magnification as FIG. 4B). Each cluster is 40-60 µm in diameter. B) Cluster of donor derived cells at 8 weeks post-transplant. Clusters are now 150-250 µm in diameter. C,D) Donor-derived cells in the larger clusters remain capillary endothelial cells. Confocal 1 µm optical section, GFP native fluorescence (green), PECAM (blue), Type I epithelium (red).

Engraftment frequency and cluster size are maintained and clusters expand with time post-transplant. Each pair of lungs from each recipient had approximately 200 clusters. The engraftment frequency was calculated as the average number of clusters per recipient divided by the number of cells injected, which is 200/70,000 equal to 0.3%. Cluster size after the first four weeks yielded 60-100 cells, and were 40-60 μm in diameter. Assuming a single cell gave rise to a cluster, each cluster represents a 60-100 fold expansion. At eight weeks post-transplant, endothelial clusters were observed to be significantly larger at >200 μm in diameter. By volume, this increase represents a>125 fold enlargement per cluster over this four week period. These larger clusters also contained contiguous GFP+ endothelial cells, as shown in FIG. 4. This result suggests that the GFP+ endothelial cells or a progenitor fraction in the cluster continue to proliferate with time.

Dose escalation does not yield an equivalent increase in number of clusters observed per recipient. 150,000 and 300,000 Sca-1+Notch1−/lo cells, representing 2× and 4× the original dose of cells, were injected into lethally irradiated recipients. We did not observe the expected 400 and 800 clusters in each respective experimental group. Instead, only ~200 clusters were observed, a number similar to the original recipients that received 70,000 of the Sca-1+Notch−/lo cells. The implications of this result is that the niche space created by radiation injury is limiting rather than the number of candidate progenitors infused.

Donor age-dependent frequency of Sca+ vs. Notch. Neonatal (3 days), juvenile (4 and 6 weeks) and adult (8 weeks) lungs were FACS analyzed for the relative frequencies of Sca-1 vs Notch1 populations. As shown in Table 2 a lower ratio of Sca-1+Notch1−/lo cells to Sca-1+Notch1+ cells was observed in older animals. Table 2 also shows that the peak of Sca-1+Notch1−/lo frequency and Sca-1+Notch1−/lo to Sca-1+Notch1+ cells was observed in the four week old animal. Based upon what is known about lung development, neonatal and juvenile lung will be enriched for EPCs. The finding that juvenile lung was especially enriched for Sca-1+Notch1−/lo cells further confirms that the Sca-1+Notch1−/lo population was enriched for alveolar specific EPCs.

Figure 5:
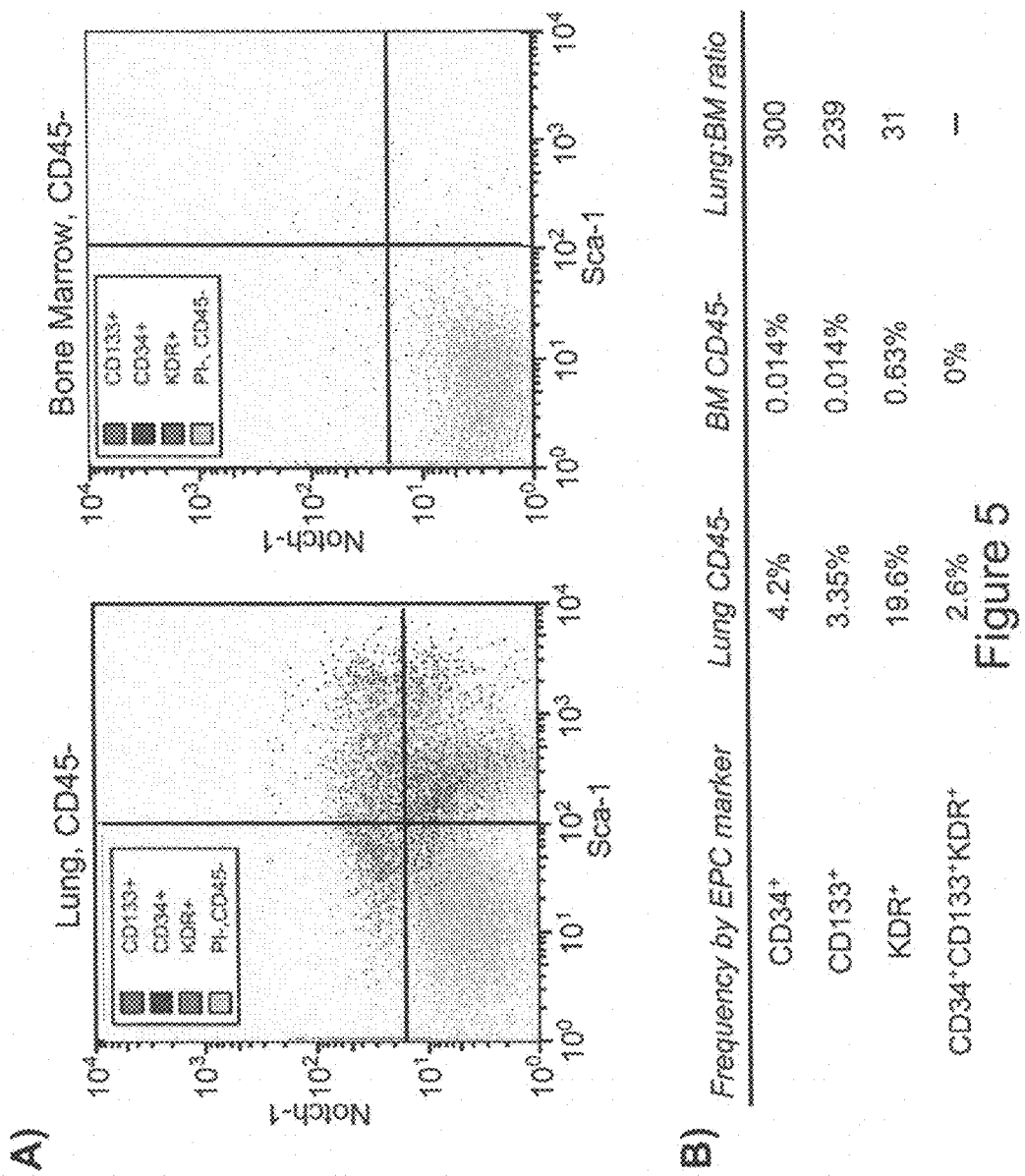
FIG. 5. EPC surface markers are highly enriched in lung vs. bone marrow. A) Six-color FACS plot of CD45$^-$ lung cells (left) and CD45$^-$ bone marrow cells (right). X-axis: Sca-1 staining. Y-axis: Notch1. Parent population cells are light blue. CD133$^+$: red. CD34$^+$: dark blue, and KDR$^+$: green. B) Table of cell frequencies.

Surface markers of endothelial progenitor cells are enriched in lung cells in comparison to bone marrow cells. We have described a lung-derived EPC population with the surface marker phenotype CD45−Sca-1+Notch1−/lo. Bone-marrow-derived EPCs have been described to express CD34 and/or CD133 and/or KDR. In order to compare the phenotype of our lung-derived EPCs with that of bone marrow-derived EPCs, 6-color FACS with Sca-1, Notch1, CD34, CD133 and KDR was used to analyze CD45− dissociated lung cells and bone marrow cells. As shown in FIG. 5A, the CD45−Sca-1+Notch1−/lo population derived from the lung contains many more cells that stain positive for the EPC markers CD34, CD133 and KDR than in the bone marrow. Lung Sca-1+Notch1−/lo cells (population E) are enriched for EPC markers and has the following frequency of markers: KDR 34-45%, CD34 0.24-0.35%, CD133 0.5-1.9%. None of the CD34+ cells are PECAM+. The relative frequency of EPCs (lung compared with bone marrow) expressing characteristic surface markers and combinations of surface markers were calculated (FIG. 5B). These data revealed that lung is enriched 30-300 fold in EPC compared to bone marrow if CD34, CD133 or KDR are putative markers of EPCs as single stains. Furthermore, unlike what we observed in lung, there were no triple-positive cells (CD34+CD133+KDR+) detected in the CD45− fraction of bone marrow. For this analysis, bone marrow was gated to be CD45−, however in studies by other investigators, CD45+ cells were included in the analysis of these EPC surface markers.

This study represents the first identification of a population of lung-derived cells capable of homing to, engrafting and expanding in injured recipient lungs in in vivo transplantation studies. The population marked by Sca-1+ and Notch1−/lo and negative for the hematopoietic marker, CD45, engrafted as uniform and contiguous clusters. These clusters exhibited the morphology of capillary endothelial

TABLE 1

Characteristics of engraftment by each population of transplanted lung cells.

| FACS population from FIG. 1C | Surface Marker Phenotype | # animals per group | # cells injected | Ave # GFP+ cell cluster (stdev) | engraftment frequency (#clusters/#cells injected × 100%) |
|---|---|---|---|---|---|
| A | CD45− Sca-1−Notch-1+ | 2 | 10,000 | 0 | 0% |
| B | CD45− Sca-1loNotch-1+ | 2 | 65,000 | 0 | 0% |
| C | CD45− Sca-1+Notch-1+ | 4 | 75,000 | 0 | 0% |
| D | CD45− Sca-1−Notch-1− | 2 | 80,000 | 0 | 0% |
| E | CD45− Sca-1+Notch-1−/lo | 4 | 70,000 | 196 (11.4) | 0.3% |

Populations A-E are defined by Sca-1 vs. Notch1 FACS analysis. Donor-derived clusters were only observed in the group of recipients that received Sca-1+Notch1−/lo cells. If each cluster is clonal, then the engraftment frequency of Sca-1+Notch1−/lo cells is 0.3%.

TABLE 2

Table 2. Frequencies of CD45−Sca-1+Notch1−/lo and CD45−Sca-1+Notch+ populations of lung cells as a function of animal age.

| Age | Frequency of Sca-1+Notch1−/lo | Frequency of Sca-1+Notch+ | Ratio of Sca-1+Notch−/lo to Sca-1+Notch1+ |
|---|---|---|---|
| Neonatal (3 days) | 19.3% | 17.7% | 1.09 |
| 4 weeks | 45.2% | 13.8% | 3.28 |
| 6 weeks | 16.3% | 31.7% | 0.51 |
| 8 weeks | 1.4% | 50.0% | 0.03 |

Lungs from ages 3 days, 4 weeks, 6 weeks, and 8 weeks were analyzed by FACS. Population frequencies are shown with the CD45− fraction as the parent population. The ratio of Sca-1+Notch1−/lo to Sca-1+Notch+ cells are shown in the last column.

cells. Although no GFP+ epithelial cells were observed in these clusters, we did observe functional recipient-derived epithelial cells overlying the GFP+ endothelial cells, suggesting that endothelial repair preceded epithelial repair. Sca-1 and Notch 1 are known to mark primitive cells in other tissues, and this finding along with the observation that lung CD45$^-$Sca-1$^+$Notch$^{-/lo}$ cells continue to extensively proliferate in areas of injury after engraftment has led us to conclude that these cells are enriched for an EPC population.

Five week old mice were used as donors in this study based upon the known developmental stages which exist in mouse lung. Microvascular maturation is the last phase of alveolization, which in mice is not completed until approximately 6 weeks after birth. When adult mice were used as a donor source of putative lung progenitor cells, almost no engraftment of donor-derived cells was observed in recipient lungs. However, when equal numbers of cells from lung donors younger than six weeks were injected, engraftment of donor-derived cells was regularly observed. Similar observations have been made in other tissues, such as bone marrow, wherein the functional hematopoietic capacity of identically surface-marked HSCs is reduced in older mice. In addition, we observed that the frequency of CD45$^-$Sca-1$^+$Notch$^{-/lo}$ cells decreased with age from juvenile to adult mice, again supporting the primitive nature of these cells, as predicted by the current understanding of lung development.

One interesting and unexpected observation was that the lung-derived Sca-1$^+$Notch$^{-/lo}$ no population homes specifically and engrafts in lung as endothelial cells. Other organs, such as gut and skin are targets for radiation injury, and therefore it might be expected that regeneration of endothelium by donor-derived cells also occur in these organs. However, we observed no donor-derived GFP+ cells in these tissues of recipients. This finding suggests that there may be tissue-specific adhesion molecules that direct endothelial or endothelial progenitor cells to specifically enter the regenerative niche of injured lung.

We hypothesize that the CD45$^-$Sca-1$^+$Notch$^{-/lo}$ population contains primitive endothelial cells that engraft as single cells and then subsequently proliferate. The expansion of cluster size and cell number with time implies that the transplanted cells maintain a high proliferative capacity, which is the hallmark of progenitor cells. Clusters at 4 weeks contained approximately 60-100 cells each. If each cluster was derived from a single cell, then that cell is capable of expanding 60-100 fold during this time period. This increase in GFP+ cells represents 6-7 doublings in 4 weeks, which is equivalent to one doubling every 3-4 days. Clusters at 8 weeks were observed to be >125 times the volume of clusters observed at 4 weeks, and this increase in volume from week 4 to week 8 is consistent with a rate of proliferation that is maintained over the first and second four-week period.

The engraftment frequency of 0.3% (# of cluster/# of cells injected) is a low number. A more accurate statement of our results can be summarized as: the CD45-Sca-1+Notch−/lo engraft in the lung at a frequency of 0.3% and the relative proportion of donor cells increases significantly with time, generating lung endothelial chimerism that is 10-15% at 8 weeks post-transplantation.

In summary, these studies demonstrate that a population derived from juvenile mouse lung can be enriched for by positive selection. These engraft as endothelial cells that home specifically to the lung, and demonstrate a high proliferative capacity. The data also suggest that lung is a superior source of EPC compared with bone marrow.

Example 2

Materials and Methods

BrdU was prepared by manufacturers (BD Biosciences) suggestion, and 100 µL was injected intraperitoneally 24 hours before harvest. A anti-BrdU antibody was directly conjugated to AlexaFluor 594 (Invitrogen) was used for immunofluorescence detection of incorporated BrdU after the histology slide had been incubated in 2M HCl for 30 min and 0.1M NaBorate for 10 min.

For the epithelial experiments, there was a four day delay between irradiation and cellular injection. A lead shield was constructed that allowed irradiation of only the right lung. Cells were delivered intra-tracheally with a 20 GA catheter that was placed in the airway via an oro-tracheal route in the recipient animal that was anesthetized with a ketamine/xylazine cocktail. The cells ($1 \times 10^5$-$4 \times 10^6$ in number) were suspended in 100 µL of an acellular surfactant prep.

Surfactant prep was obtained from donor mice on the same day as intra-tracheal transplants. Serial aliquots of 1 mL (PBS) each were infused endotracheally and lavaged in and out of the tracheal catheter 5 times per aliquot. The aliquots were then pooled and centrifuged to remove the cellular component.

Figure 7:
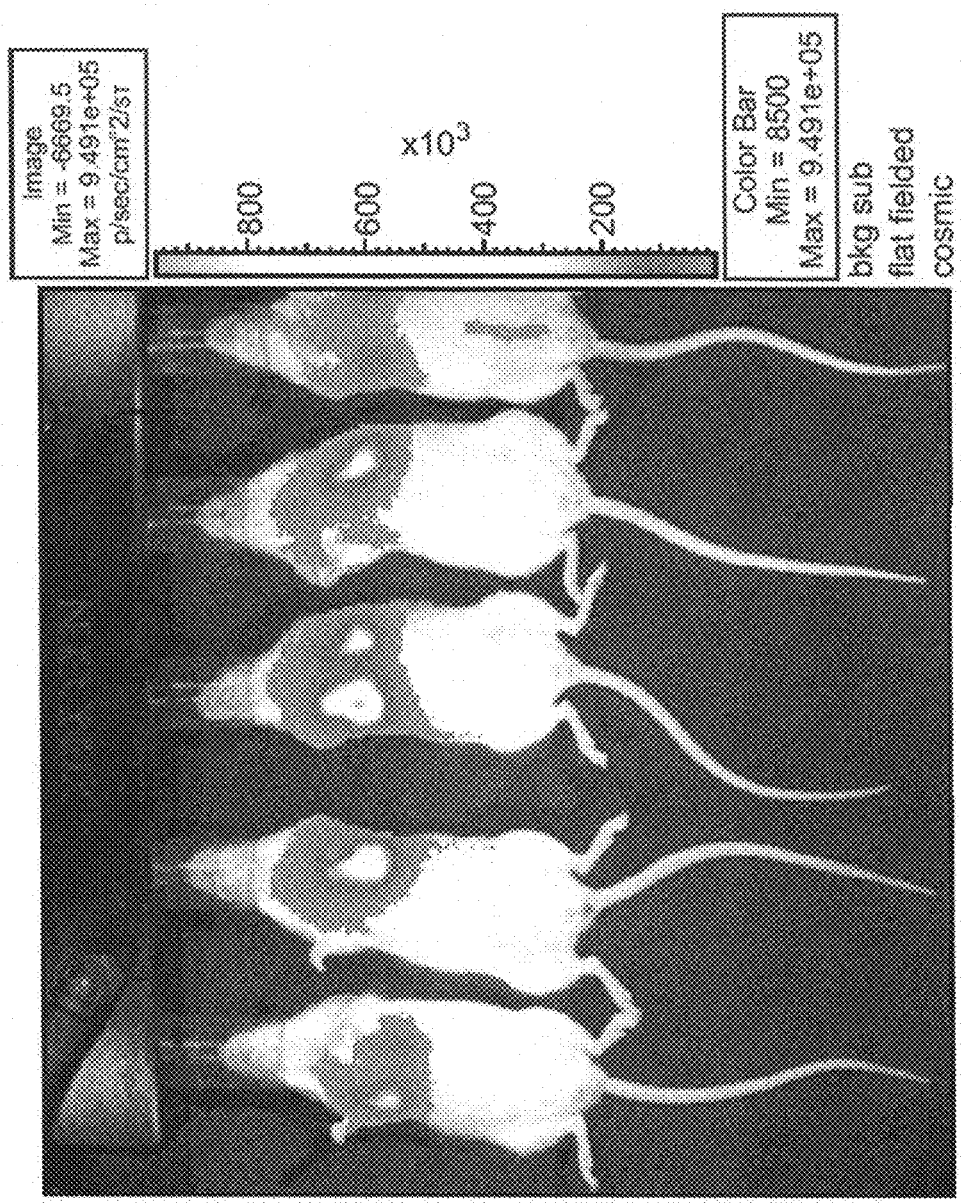
FIG. 7. Characterization of CD45$^-$Sca-1$^+$Notch1$^{-/lo}$ cells following transplantation. animals were pulsed with BrdU for 24 hours before harvest of lungs for histology.

Results and Discussion:

Characterizing proliferation—BrdU pulse. At six weeks post-transplant of CD45$^-$Sca-1$^+$Notch1$^{-/lo}$ cells, animals were pulsed with BrdU for 24 hours before harvest of lungs for histology. As shown in FIG. 7, BrdU+ nuclei were much more frequently observed in the GFP+ endothelial clusters. In fact, clusters of BrdU+ nuclei were only observed in the area of lung where there were clusters of GFP+ endothelial cells. There are BrdU+ nuclei that colocalize with GFP+ endothelial cells, but there are also host-derived (GFP−) cells that colocalize with BrdU+ nuclei. Many of these host-derived BrdU+ cells are epithelial cells (epithelial marker immunofluorescence not shown). This is definitive proof that the endothelial progenitor cells continue to proliferate in vivo. The label of progenitor cell is appropriate because the ability to proliferate and yield terminally differentiated cells is the central functional definition of a progenitor cell. Furthermore, from the observation that BrdU+ nuclei only are in and around GFP+ cells, it appears that endothelial repair induces the repair or turnover of adjacent epithelial cells. This has important implications for the essential sequence of events necessary for alveolar repair.

Figure 8:
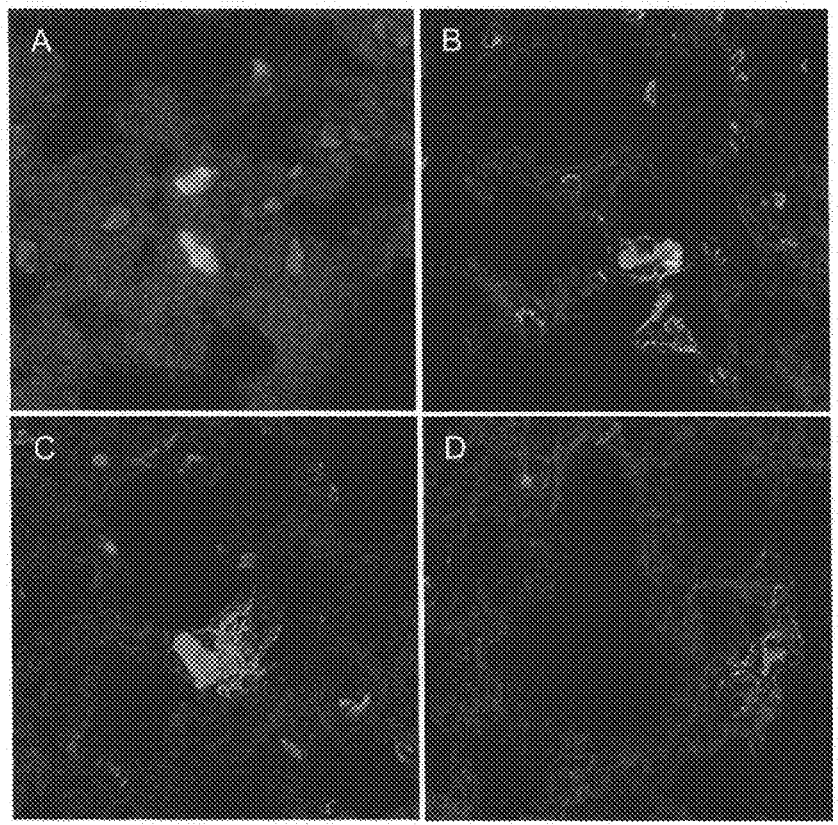
FIG. 8 shows a demonstration of epithelial engraftment where luciferase$^+$CD45$^-$ cells were injected intratracheally and shown to continue to be viable in the lung by bioluminescence imaging.
Figure 9:
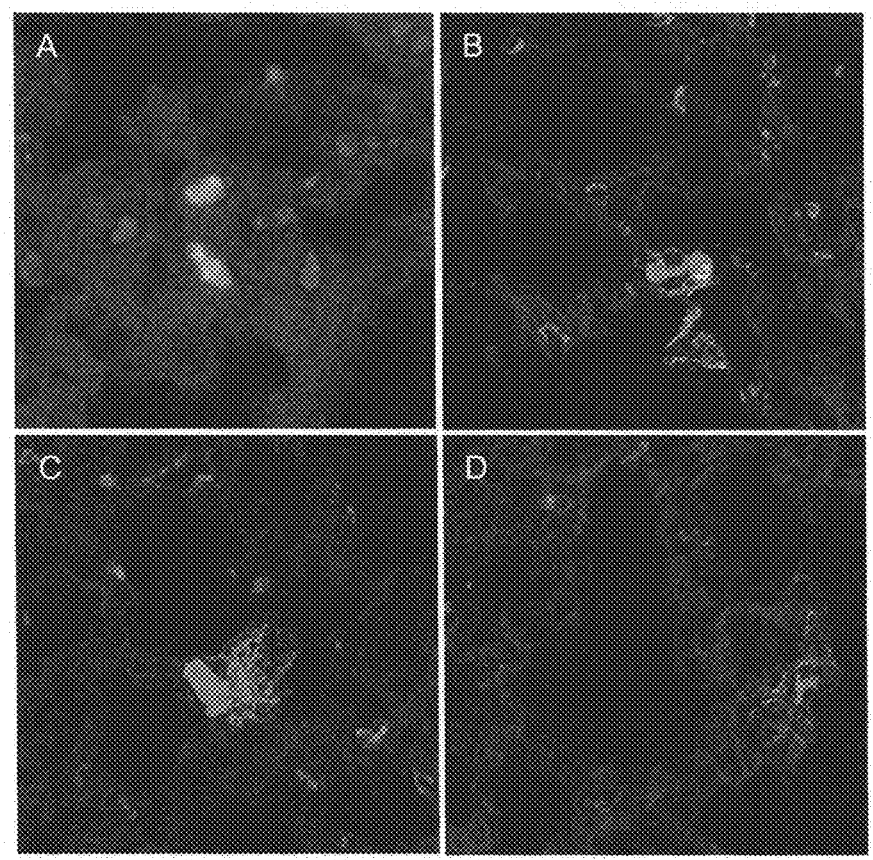
FIG. 9 shows the different epithelial progenitor populations and their engraftment patterns as alveolar epithelial cells.

Epithelial engraftment. A similar in vivo screen of surface markers to identify alveolar epithelial progenitor cells was initiated. FIG. 8 shows a demonstration where Luciferase+ CD45− cells were injected intratracheally and shown to continue to be viable in the lung by bioluminescence imaging. FIG. 9 shows the different epithelial progenitor populations and their engraftment patterns as alveolar epithelial cells.

Two separate engrafting populations were identified. CD45$^-$Sca-1$^-$ cells initially engraft as Type II epithelial cells at 4 weeks post-transplant, but then generate Type I epithelial cells as well 8 weeks post-transplant. $1 \times 10^6$ CD45$^-$Sca-1$^-$ cells were injected intratracheally four days after right lung irradiation. GFP+ cells co-localize with pro-SPC, a Type II epithelial cell marker, at four weeks transplant. GFP+ cells were frequently seen in proximity (within one alveolus) as shown (FIG. 9A), suggesting co-migration or in vivo proliferation.

However, at 8 weeks post-transplant, a different pattern was seen. Usually, at the center of each GFP+ cluster, there was a GFP+ cell that colocalized with pro-SPC, suggesting that it is a Type II epithelial cell. Surrounding this cell are cells that are very thin (lack of cytoplasm yields less intense cytoplasmic GFP fluorescence, FIG. 9B). These thin GFP+ cells colocalize with T1α, a Type I epithelial cell marker. The different epithelial lineages of engraftment of the CD45−Sca-1− cells at 4 vs. 8 weeks suggests that the engrafting cells are Type II epithelial cells with progenitor cell capacity for differentiating into Type I cells.

Another engrafting population was identified. The composite surface marker phenotype used was CD45−PECAM−T1α+. We observed two different patterns of engraftment at 8 weeks post-transplant. First, a similar pattern was observed to the CD45− Sca-1− cells, where there were clusters with a central cell that co-localized with SPC and surrounding cells that colocalized with T1α (FIG. 9C). However, there was a second pattern of engraftment as well, where there was no central GFP+SPC+ cell, but only a cluster of GFP+T1a+ cells (FIG. 9D).

These results show that epithelial progenitor cells can be delivered to the distal lung (alveolar compartment) via an endotracheal route. This has not been shown previously and represents a novel delivery technique to the epithelial surface of the alveolus. This type of delivery was only shown to be effective for proximal airway epithelia. We believe the use of surfactant prep as a vehicle is the essential component that leads to droplets small enough to travel to the alveolar space.

There are two distinct populations of cells enriched for alveolar epithelial cells that show overlapping yet distinct patterns of engraftment: These results are consistent with models of the sequence of differentiation and progenitor identity in alveolar epithelium.

What is claimed is:

1. An enriched composition of mammalian lung epithelial progenitor cells, wherein the cells in said composition are selected from a cell suspension of lung tissue using reagents that specifically recognize the marker CD45; PECAM; and T1a; at least 80% of the cells in said composition are characterized as CD45−PECAM−T1a+; and the CD45−PECAM−T1a+ cells are capable of giving rise to Type I and Type II alveolar epithelial cells, wherein said cells comprise an exogenous gene incorporated into the genome of the cell.

2. The composition according to claim 1, wherein said lung tissue comprises post-natal cells.

3. The composition according to claim 1, wherein said lung tissue comprises pre-natal cells.

* * * * *